(12) United States Patent
Davis et al.

(10) Patent No.: US 11,918,572 B2
(45) Date of Patent: Mar. 5, 2024

(54) PHARMACEUTICAL COMPOSITIONS FOR TREATING PAIN

(71) Applicant: REBEL MEDICINE INC, Salt Lake City, UT (US)

(72) Inventors: Brett Hale Davis, Salt Lake City, UT (US); Caleb Adrian Lade, Salt Lake City, UT (US); Sierra Nichelle Erickson, Salt Lake City, UT (US); Susan Alice Wojtalewicz, Salt Lake City, UT (US)

(73) Assignee: REBEL MEDICINE INC, Salt Lake City, UT (US)

( * ) Notice: Subject to any disclaimer, the term of this patent is extended or adjusted under 35 U.S.C. 154(b) by 0 days.

(21) Appl. No.: 18/160,874

(22) Filed: Jan. 27, 2023

(65) Prior Publication Data

US 2023/0241048 A1 Aug. 3, 2023

Related U.S. Application Data

(60) Provisional application No. 63/267,256, filed on Jan. 28, 2022.

(51) Int. Cl.
| | | |
|---|---|---|
| *A61K 31/277* | (2006.01) | |
| *A61K 31/445* | (2006.01) | |
| *A61K 47/14* | (2017.01) | |
| *A61K 47/44* | (2017.01) | |
| *A61P 23/02* | (2006.01) | |

(52) U.S. Cl.
CPC ............ *A61K 31/445* (2013.01); *A61K 47/14* (2013.01); *A61K 47/44* (2013.01); *A61P 23/02* (2018.01)

(58) Field of Classification Search
None
See application file for complete search history.

(56) References Cited

U.S. PATENT DOCUMENTS

| | | |
|---|---|---|
| 2018/0344663 A1 | 12/2018 | Vu et al. |
| 2019/0231762 A1 | 8/2019 | Verity |
| 2021/0106707 A1 | 4/2021 | Shodder |

FOREIGN PATENT DOCUMENTS

| | | | |
|---|---|---|---|
| CN | 102973494 A | * 3/2013 | |
| CN | 113827547 | 12/2021 | |
| WO | WO-2010079443 A1 | * 7/2010 | ........... A61K 31/427 |

OTHER PUBLICATIONS

Davis et al. (Entrapping bupivacaine-loaded emulsions in a crosslinked-hydrogel increases anesthetic effect and duration in a rat sciatic nerve block model. International Journal of Pharmaceutics vol. 588, Oct. 15, 2020, 119703.*
"International Application Serial No. PCT US2023 061464, International Search Report dated May 3, 2023", 2 pgs.
"International Application Serial No. PCT US2023 061464, Written Opinion dated May 3, 2023", 10 pgs.

* cited by examiner

*Primary Examiner* — Layla Soroush
(74) *Attorney, Agent, or Firm* — Schwegman Lundberg & Woessner, P.A.

(57) ABSTRACT

A pharmaceutical composition can include a lipophilic oil. The pharmaceutical composition can further include an analgesic agent, anesthetic agent, anti-inflammatory agent, or a mixture thereof dispersed in the lipophilic oil. The pharmaceutical composition can further include a structuring agent at least a portion of which is not dissolved in the lipophilic oil and forms a gel.

5 Claims, 13 Drawing Sheets

PHARMACEUTICAL COMPOSITIONS FOR TREATING PAIN

CROSS-REFERENCE TO RELATED APPLICATION

This application claims the benefit of priority to U.S. Provisional Patent Application Ser. No. 63/267,256 entitled "PHARMACEUTICAL COMPOSITIONS FOR TREATING PAIN," filed Jan. 28, 2022, the disclosure of which is incorporated herein in its entirety by reference.

BACKGROUND

Local anesthetics are widely used in surgery to anesthetize the surgical site and to reduce postoperative pain, but because of their short durations of effect, they are unable to provide analgesia throughout the period when patients experience severe pain. When the anesthetic wears off, opioid medications are given to manage this pain, most often for three or more days, until less potent analgesics are able to control the pain.

SUMMARY OF THE DISCLOSURE

A problem that the instant disclosure seeks to solve is to provide an injectable or implantable composition that can provide 2-14 days of robust pain relief that is both injectable and viscous enough to be manually implanted into a surgical site and remain at the administration site long enough to provide a local anesthetic effect. The disclosure therefore relates to a pharmaceutical composition, comprising:
  a lipophilic oil;
  a drug, salt, or prodrug thereof (e.g., an analgesic agent, anesthetic agent, anti-inflammatory agent, or a mixture thereof dispersed in the lipophilic oil; and
  a structuring agent at least a portion of which is not dissolved in the lipophilic oil and forms a gel.
The disclosure also relates to a pharmaceutical composition, comprising:
  a medium-chain triglyceride;
  an anesthetic agent comprising bupivacaine, ropivacaine, or both and present in amount sufficient to reduce pain in a subject, and dispersed about the medium-chain triglyceride; and
  a structuring agent comprising tristearin, glyceryl distearate, glycerol monostearate, glyceryl dibehenate, cholesterol, trimyristin, glyceryl dimyristin, glyceryl monomyristin, trilaurin, glyceryl dilaurin, glyceryl monolaurin, tripalmitin, glyceryl dipalmitin, glyceryl monopalmitin, cholesterol, a polyglyceride ester of a fatty acid, a polyglycerol ester of a fatty acid, or a mixture thereof.
The disclosure relates to a kit comprising:
  a syringe; and
  the pharmaceutical composition of the disclosure disposed within the syringe.
The disclosure also relates to a method of manufacturing a pharmaceutical composition, the method comprising:
  a) mixing the lipophilic oil and the analgesic agent, anesthetic agent under stirring at a temperature above 25° C. to form a first mixture;
  b) mixing the structuring agent with the first mixture under stirring and heating at a temperature above 25° C. to form a second mixture; and
  c) cooling the second mixture to form the pharmaceutical composition.

The disclosure relates to a method of treating a subject with a composition of the disclosure, comprising administering the composition to the subject in need thereof.

BRIEF DESCRIPTION OF THE FIGURES

The drawings illustrate generally, by way of example, but not by way of limitation, various embodiments of the present disclosure.

DETAILED DESCRIPTION OF THE DISCLOSURE

Figure 1:
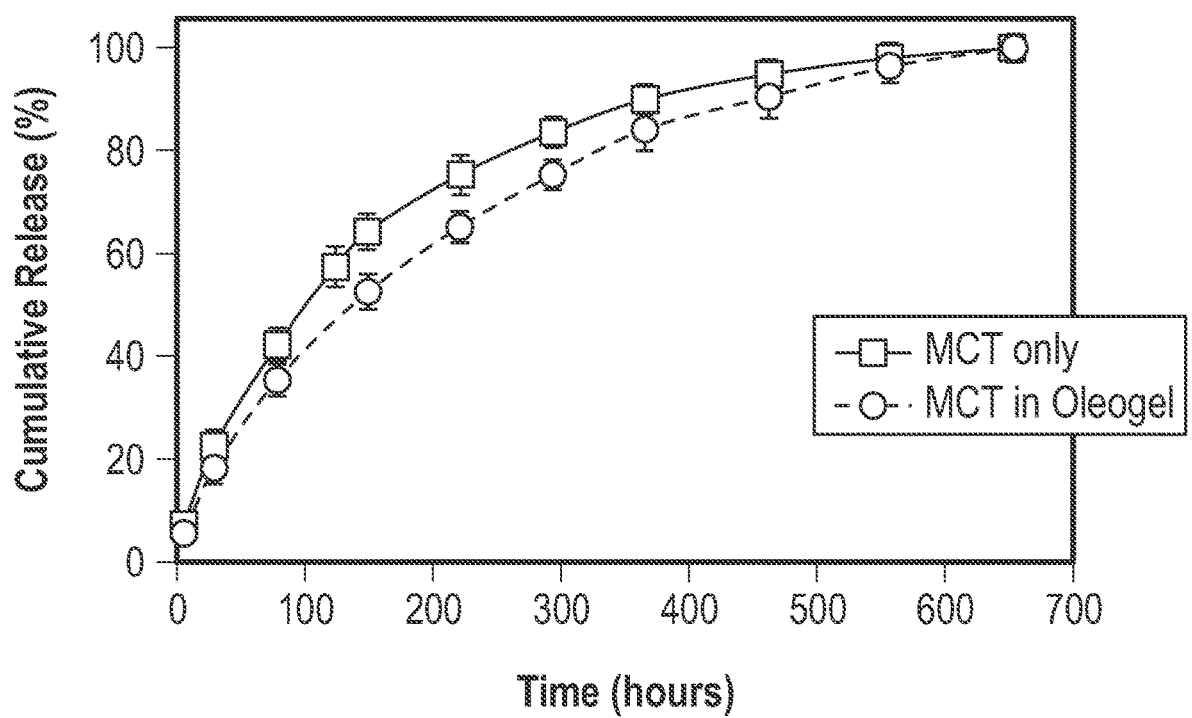
FIG. 1 is a graph showing drug release profiles of various oils.

Reference will now be made in detail to certain aspects of the disclosed subject matter. While the disclosed subject matter will be described in conjunction with the enumerated claims, it will be understood that the exemplified subject matter is not intended to limit the claims to the disclosed subject matter.

The present disclosure relates to a pharmaceutical composition comprising a lipophilic oil component; a therapeutic agent, or a mixture thereof dispersed in the lipophilic oil component; and a structuring agent, at least a portion of which is not dissolved in the lipophilic oil. These components can form a semi-solid oleogel consisting of drug-loaded lipophilic oil entrapped in a supramolecular network of self-assembled structures, for example, molecular aggregates, crystals, and the like. The pharmaceutical composition can be used in both human and veterinary pain management applications. Possible clinical uses include, but are not limited to, neuraxial, regional and local anesthesia for the treatment of procedural, postoperative, and injury-related pain, local infiltrative anesthesia for myofascial pain (e.g., trigger points), and chronic pain.

The pharmaceutical compositions described herein can be used for post-operative pain management as a substitute for drugs used for post-operative pain management that include an opioid. The described pharmaceutical composition can be a complete substitution for the drug including an opioid or it can be used in conjunction with a drug including an opioid to reduce the amount of the opioid used in post-operative pain management.

The composition can take the form of an injectable semi-solid gel, paste, or implantable solid. In the form of a semi-solid gel or paste, the composition can be applied to a surgical site/wound, and because of its viscosity, the gel remains where initially applied. Upon closing the surgical site/wound, the semi-solid gel can intercalate within natural crevices and smear between compressed tissues. The self-assembled supramolecular network created by the structuring agent prevents the drug-oil phase from migrating away from the site of administration, which facilitates safer and more effective localized treatment. The structuring agent network also shields the drug-loaded oil from the surrounding in vivo environment (e.g., a surrounding aqueous in vivo environment) which enables the prolonged diffusion-based drug release from the oil into the aqueous environment. The composition can be biodegradable and can, therefore, be naturally resorbed by the body over time.

Depending on the concentration and unique properties of the structuring agent, the composition can be tuned to have various mechanical properties. Tuning of the mechanical properties is relevant to creating a long-acting local anesthetic drug product that represents an improvement to many of the current clinically available technologies. If the mechanical properties are too robust, the composition may not be injectable through small bore needles (e.g., >23 gauge), which would only allow it to be manually implanted into a surgical wound cavity. For some long-acting local anesthetic products for postoperative pain, the mechanical properties need to be optimized so that it can be injectable through an acceptable needle size (18-25 gauge) but remains viscous enough so it is retained at the site of implantation.

The structuring agent is useful to provide adequate structure and mechanical properties to the composition. For example, if the therapeutic agent or drug (e.g., analgesic agent, anesthetic agent, anti-inflammatory agent, or a mixture thereof) is simply loaded into a plain lipophilic oil carrier (e.g., medium-chain triglycerides), the resulting solution will be thin and flowable liquid like an aqueous solution. Therefore, if the solution (lacking the structuring agent) is injected or implanted directly into a surgical wound cavity, the solution can migrate and be eliminated from the site of administration, therefore lowering its effectiveness of controlling the pain at the target site. Additionally, rapid elimination of the drug will increase the risk of systemic toxicity (e.g., cardiotoxicity or neurotoxicity), which can be life-threatening. Therefore, as an example, an advantageous long-acting local anesthetic composition should be both injectable and viscous enough to be manually implanted into a surgical site. Some current clinically available options include solid, implantable technologies that can only be implanted into surgical sites, which significantly limits their clinical applications. Injectable compositions can be used as prolonged duration nerve blocks for regional anesthesia, a technique which has become widely popular for the non-opioid management of postoperative pain; however, the current injectable options only last for less than 24 hours. Therefore, a problem that the instant disclosure seeks to solve is to provide a safe injectable or implantable composition that can provide 2-14 days of robust pain relief (e.g., analgesic effect) that is both injectable and viscous enough to be manually implanted into a surgical site, while also being able to remain at the site it is implanted to for an amount of time sufficient to provide a local analgesic effect.

The lipophilic oil of the composition can be chosen from many suitable oils. For example, the lipophilic oil can include a monoglyceride, diglyceride, triglyceride, sesame oil, soybean oil, castor oil, tributyrin oil, vegetable oil, or a mixture thereof. For example, the lipophilic oil can include a mixture of a medium chain triglyceride oil and castor oil in which either independently ranges from 5 wt % to 98 wt %, 30 wt % to 70 wt %, less than, equal to, or greater than 5 wt %, 10, 15, 20, 25, 30, 35, 40, 45, 50, 55, 60, 65, 70, 75, 80, 85, 90, or about 98 wt %. Sesame oil generally includes 41 wt % linoleic acid, 39 wt % oleic acid, 8 wt % palmitic acid, 5 wt % stearic acid, and trace amounts of other organic acids. Per 100 g, soybean oil has 16 g of saturated fat, 23 g of monounsaturated fat, and 58 g of polyunsaturated fat. The major unsaturated fatty acids in soybean oil triglycerides are 7 to 10 wt % polyunsaturated alpha-linolenic acid, and 51 wt % linoleic acid, and 23 wt % monounsaturated oleic acid. Soybean oil also includes saturated fatty acid such as 4 wt % stearic acid and 10 wt % palmitic acid. Castor oil includes 85 to 95 wt % ricinoleic acid, 2 to 6 wt % oleic acid, 1 to 5 wt % linoleic acid, 0.5 to 1 wt % $\alpha$-linolenic acid, 0.5 to 1 wt % stearic acid, 0.5 to 1 wt % palmitic acid, 0 to 0.5 wt % dihydroxystearic acid, and 0.2 to 0.5 wt % additional compounds. The tributyrin oil is an ester that is a reaction product of butyric acid and glycerol. The triglyceride can be a medium-chain triglyceride, a short-chain triglyceride, or both. Examples of medium-chain triglycerides include an ester that is a reaction product glycerol with any of a C6-C12 carboxylic acid (e.g., hexanoic acid, octanoic acid, decanoic acid, lauric acid, or a mixture thereof).

Medium-chain triglycerides can be particularly well suited as the lipophilic oil. While not intending to be limited to any theory, the benefits of using medium-chain triglycerides are believed to be due to their thin nature and low viscosity, each of which makes it injectable (as compared to castor oil, which has good drug solubility but is very viscous). Additionally, medium-chain triglycerides are shown to accommodate high drug loading and good rates of release. Therefore, medium-chain triglycerides are beneficial in that they exhibit a viscosity that allows it to be injectable, structured to a supramolecular gel using a structuring agent, loaded with a sufficient amount of a drug, and exhibits a good drug release profile.

A mixture of lipophilic oils can be used. For example, the pharmaceutical composition can include a mixture of medium-chain triglycerides and short-chain triglycerides, medium-chain triglycerides and long-chain triglyceride oils, or short-chain triglycerides and long-chain triglycerides. In some examples the solubility of drugs such as ropivacaine can be increased in a mixture of medium-chain triglycerides and short-chain triglycerides at a 90:10 (medium-chain triglyceride: short-chain triglyceride). As a further example a mixture medium-chain triglycerides and castor oil as the lipophilic oil will achieve a higher drug load with reducing viscosity in the overall structure.

The structuring agent (alternatively referred to as an organostructuring agent, oleostructuring agent, or supramolecular structuring agent) imparts a structure to the lipophilic oil. For example, the structuring agent helps to form a gel. An example of a type of gel is a supramolecular gel is a complex of molecules held together by noncovalent interactions such as H-bonding, Pi-Pi interactions, anionic-Pi interactions, cationic-Pi interactions, and van der Waals forces. The process by which a supramolecular assembly forms is called molecular self-assembly. Molecular self-assembly refers to the process by which molecules adopt a defined arrangement without guidance or management from an outside source.

The structuring agent is present in a concentration in a range of from about 0.1% (w/v) to about 25% (w/v) of the pharmaceutical composition based on the volume of the lipophilic oil, about 5% (w/v) to about 25% (w/v), about 10% (w/v) to about 15% (w/v), about 5% (w/v) to 10% (w/v), about 5% (w/v) to 15% (w/v), about 10% (w/v) to 20% (w/v), less than, equal to, or greater than about 0.1% (w/v), 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, or about 25% (w/v). The structuring agent or mixture of structuring agents used can depend on several factors such as the melting point of the structuring agent. For example, a melting point of the structuring agent can be in a range of from about 40° C. to about 100° C., about 50° C. to about 85° C., about 45° C. to about 60° C., about 50° C. to about 70° C., less than, equal to, or greater than about 40° C., 45, 50, 55, 60, 65, 70, 75, 80, 85, 90, 95, or about 100° C.

Examples of suitable structuring agents include a monoglyceride, a diglyceride, a triglyceride, a polyglycerol ester of a fatty acid, or a mixture thereof. Polyglycerols used herein can be a diglycerol or triglycerol and can be fully or partially esterified with saturated or unsaturated fatty acid moieties. The fatty acid can include caprylic acid (C8), capric acid (C10), lauric acid (C12), myristic acid (C14), palmitic acid (C16), stearic acid (C18), arachidonic acid (C20), behenic acid (C22), or a mixture thereof. More specific examples of suitable structuring agents include tristearin, glyceryl distearate, glycerol monostearate, glyceryl dibehenate, cholesterol, trimyristin, glyceryl dimyristin, glyceryl monomyristin, trilaurin, glyceryl dilaurin, glyceryl monolaurin, tripalmitin, glyceryl dipalmitin, glyceryl monopalmitin, diglycerol esterified with stearic acid, cholesterol, or a mixture thereof.

At least a portion of the structuring agent is phase separated in the lipophilic oil. Thus, for example, a portion of the structuring agent can be partially dissolved in the lipophilic oil (first phase), while a second portion is not dissolved in the lipophilic oil (second phase). The phase separation of the structuring agent allows the structuring agent to help the pharmaceutical composition achieve the supramolecular gel within the lipophilic oil. If the structuring agent is too soluble in the lipophilic oil, it will dissolve therein and the supramolecular gel cannot be formed. If the structuring agent is too insoluble, it will not interact with the lipophilic oil and the pharmaceutical composition will take the form of a heterogenous unstable gel with the structuring agent precipitated out.

The supramolecular gel itself can be characterized as a semi-solid composition (alternatively referred to as a quasi-solid or a semiliquid). While similar to solids in some respects, such as having the ability to support their own weight and hold their shapes, a semi-solid composition also shares some properties of liquids, such as conforming in shape to something applying pressure to it and the ability to flow under pressure. Selecting the proper structuring agent also impacts the viscosity of the pharmaceutical composition. A proper viscosity allows the pharmaceutical composition to substantially remain in a desired location in the body. An example of a suitable viscosity at 37° C. is in the range of about 1,000 cP to about 1,000,000 cP, about 100,000 cP to about 1,000,000 cP, about 5,000 cP to about 200,000 cP, about 10,000 cP to about 100,000 cP, about 50,000 cP to about 150,000 cP, about 10,000 cP to about 500,000 cP, 20,000 cP to about 90,000 cP, less than, equal to, or greater than about 10,000, 15,000, 20,000, 25,000, 30,000, 35,000, 40,000, 45,000, 50,000, 55,000, 60,000, 65,000, 70,000, 80,000, 85,000, 90,000, 95,000, 100,00, 105,000, 110,000, 115,000, 120,000, 125,000, 130,000, 135,000, 140,000, 145,000, 150,000, 155,000, 160,000, 165,000, 170,000, 175,000, 180,000, 185,000, 190,000, 195,000, 200,000, 205,000, 210,000, 215,000, 220,000, 225,000, 230,000, 235,000, 240,000, 245,000, 250,000, 255,000, 260,000, 265,000, 270,000, 275,000, 280,000, 285,000, 290,000, 295,000, 300,000, 305,000, 310,000, 315,000, 320,000, 325,000, 330,000, 335,000, 340,000, 345,000, 350,000, 355,000, 360,000, 365,000, 370,000, 375,000, 380,000, 385,000, 390,000, 395,000, 400,000, 405,000, 410,000, 415,000, 420,000, 425,000, 430,000, 435,000, 440,000, 445,000, 450,000, 455,000, 460,000, 465,000, 470,000, 475,000, 480,000, 485,000, 490,000, 495,000, 500,000, 600,00, 605,000, 610,000, 615,000, 620,000, 625,000, 630,000, 635,000, 640,000, 645,000, 650,000, 655,000, 660,000, 665,000, 670,000, 675,000, 680,000, 685,000, 690,000, 695,000, 700,000, 705,000, 710,000, 715,000, 720,000, 725,000, 730,000, 735,000, 740,000, 745,000, 750,000, 755,000, 760,000, 765,000, 770,000, 775,000, 780,000, 785,000, 790,000, 795,000, 800,000, 805,000, 810,000, 815,000, 820,000, 825,000, 830,000, 835,000, 840,000, 845,000, 850,000, 855,000, 860,000, 865,000, 870,000, 875,000, 980,000, 985,000, 990,000, 995,000, 1,000,000 cP.

If the viscosity is too low, the pharmaceutical composition will disperse beyond the desired location. Additionally, if the viscosity is too low, an uncontrolled release of the drug can result. Conversely, if the viscosity is too high, it can be impossible to inject the pharmaceutical composition to the desired location. This may leave manual application (e.g., by hand or using an instrument to apply or spread the composition to the site) as the only viable option. However, even manual application may be impractical if the viscosity is too high. The viscosities required to maintain material retention at the application site are generally too high to enable injection through clinically relevant needle sizes (18 g-25 g needles). A particular disadvantage to not being able to inject through these needles is that such solutions cannot be used as a nerve block. To overcome this, the pharmaceutical compositions disclosed are engineered to be shear-thinning, which is defined as the ability of a material to decrease in viscosity with increasing shear. Such compositions can be pre-loaded into syringes, extruded upon application of shear, and regain their viscosities upon cessation of mechanical load, a process known as self-healing. This self-healing behavior allows for both improved application and material retention thus improving the usefulness and efficacy of the pharmaceutical product while also exhibiting the prolonged drug release characteristics described herein. As an example, when sheared at sweeps ranging from 0.01 hz to 200 hz, the viscosities at 37° C. can go as low as about 10 cP to about 10,000 cP, about 20 cP to about 5,000 cP, about 20 cP to about 500 cP, less than, equal to, or greater than about 10 cP, 100, 200, 300, 400, 500, 600, 700, 800, 900, 1,000, 2,000, 3,000, 4,000, 5,000, 6,000, 7,000, 8,000, 9,000, or about 10,000 cP. Unless otherwise specified, all viscosity values described herein are obtained at 37° C., by a HAAKE Mars 60 rheometer, available from Thermo-Fisher Scientific, Waltman MA.

The drug can be present in the pharmaceutical composition in a therapeutically effective amount. A "therapeutically effective amount" (or "effective amount") of a compound with respect to use in treatment, refers to an amount of the compound in a preparation which, when administered as part of a desired dosage regimen (to a mammal, such as a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the patient of one or more compound of the disclosure. If it is administered prior to clinical manifestation of the unwanted condition (e.g., disease or other unwanted state of the host animal) then the treatment is prophylactic, (e.g., it protects the host against developing the unwanted condition), whereas if it is administered after manifestation of the unwanted condition, the treatment is therapeutic, (e.g., it is intended to diminish, ameliorate, or stabilize the existing unwanted condition or side effects thereof).

The exact amount of the drug can vary and is selected depending on the application. As a non-limiting example, the drug can be present in a concentration in a range of from about 0.5% (w/v) to about 40% (w/v), about 1% (w/v) to about 25% (w/v), 2% (w/v) to about 15% (w/v) based on a volume of the lipophilic oil, about 3% (w/v) to about 10% (w/v), about 5% (w/v) to about 8% (w/v), less than, equal to, or greater than about 0.5% (w/v), 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, or about 40% (w/v), based on the volume of the lipophilic oil. Whether an amount is therapeutically effective can be a factor of the amount of time that pain is reduced in a subject. For example the pharmaceutical composition may be effective to reduce pain in vivo in a subject for a time in a range of from about 24 hours to about 14 days, 48 hours to about 14 days, from about 72 hours to about 96 hours, from about 72 hours to about 80 hours, less than, equal to, or greater than about 24 hours, 25 hours, 26 hours, 27 hours 28 hours, 29 hours 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours, 51 hours, 52 hours, 53 hours, 54 hours, 55 hours, 56 hours, 57 hours, 58 hours, 59 hours, 60 hours, 61 hours, 62 hours, 63 hours, 64 hours, 65 hours, 66 hours, 67 hours, 68 hours, 69 hours, 70 hours, 71 hours, 72 hours, 73 hours, 74 hours, 75 hours, 76 hours, 77 hours, 78 hours, 79 hours, 80 hours, 81 hours, 82 hours, 83 hours, 84 hours, 85 hours, 86 hours, 87 hours, 88 hours, 89 hours, 90 hours, 91 hours, 92 hours, 93 hours, 94 hours, 95 hours, 96 hours, 5 days, 6 days, 7 days, 8 days, 9 days, 10 days, 11 days, 12 days, 13 days, or about 14 days. Some pharmaceutical compositions can be designed to be effective to reduce pain for specified ranges such as 12 hours to 48 hours, 48 hours to 96 hours, 96 hours to 144 hours, 144 hours to 240 hours, or 240 hours to 336 hours. The exact drug release characteristics can be a function of the structure of the pharmaceutical composition. For example, a specific blend of lipophilic oils affects drug release characteristics. For example, a specific ion pair (e.g., lipophilic salt) formed with the therapeutic agent can affect the release characteristics.

The amount of time that that the pharmaceutical composition is therapeutically effective can be a result of the release rate of the drug from the lipophilic oil. The drug release from lipophilic oil is controlled by diffusion. Depending on the drugs affinity to the specific lipophilic oil or specific blend of lipophilic oils, the drug will preferentially reside in the lipophilic oil and slowly diffuse into the surrounding aqueous medium in a patient's body depending on its greater affinity to the lipophilic oil than the aqueous medium. The drug release rate is also dependent on the interfacial area between the oil-based carrier and the surrounding aqueous in vivo environment. The aforementioned interfacial area can be controlled by the supramolecular gel provided by the structuring agent. Without any structure, the pharmaceutical composition can freely flow and spread in vivo, this drastically increases its interfacial surface area and, therefore, drastically accelerates its drug release rate. However, if the lipophilic oil is formed into a viscous semi-solid by its supramolecular gel, it will have a significantly reduced ability to spread and increase its interfacial area, therefore reducing the rate of drug release and prolonging the effect of locally controlled non-opioid pain management (if the drug is used as an analgesic or anesthetic agent).

The therapeutic agent comprises an analgesic agent, anesthetic agent, anti-inflammatory agent. Therapeutic agents of various lipophilicity in their base form can be covalently or non-covalently modified to improve their lipophilicity and resultant solubility and drug loading capacity in the base oil. This is achieved by altering the physicochemical properties of the drug (e.g, melting point, polarity, hydrophobicity, partition coefficient). Using covalent modification, prodrugs of the agents can be synthesized that are significantly more lipophilic and suitable for use in the disclosed composition. This can also be achieved using non-covalent modification. For example, hydrophobic ion pairing can be used to ionically pair charged drug molecules with oppositely-charged molecules with hydrophobic moieties. The resultant complexes are more lipophilic and hydrophobic allowing better encapsulation into and more controlled release from lipid-based formulations. Both covalent and non-covalent modulation of the drug can thus be used to tune drug release of naturally lipophilic or naturally hydrophobic drugs from the system. The desired solubility and partition coefficients from the base oil will be different for different drugs and intended uses. For example, a drug having a log P of less than 2 could be modified by the formation of a prodrug that makes the log P greater than the recited log P values (e.g., at least 2). These examples of covalent and non-covalent chemical modification increase the lipophilicity leading to greater affinity to the base oil leading to slower modified release characterisitics. In such an example, the drug having a log P of less than 2 can comprise a hydroxy or amino functional group that can form an ester or an amide, respectively, with a $C_{12}$-$C_{22}$-carboxylic acid. The resulting $C_{12}$-$C_{22}$-ester or amide may have the recited log P values (e.g., at least 3). Alternatively, or in addition, the drug or prodrug can be modified by pairing it with a hydrophobic counterion that may have the recited log P values. For example, the drug or prodrug can be synthesized to be a docusate salt or can be ion exchanged to form a docusate salt, where the docusate is the counterion of the drug. Other such counterions are known in the art and are contemplated herein. Accordingly, in addition to the analgesic agents, anesthetic agents, and anti-inflammatory agents described herein, the pharmaceutical compositions described herein can also be formulated to contain one or more adjuvant agents, which may also be covalently or non-covalently modified. Examples include, but are not limited to, sympatholytic agents (e.g., dexmedetomidine, clonidine), anxiolytic agents (e.g., midazolam), anti-inflammatory agents (e.g., dexamethasone, NSAIDs, COX-2 inhibitors), and cannabinoids (e.g., cannabidiol).

As used herein, the partition coefficient, or log P, is a measure of the lipophilicity of a drug and an indication of its ability to cross the cell membrane. It is defined as the ratio between drug distributed between the organic and aqueous layers at equilibrium. The partition coefficient of a drug may be determined by shaking it with equal parts of two immiscible solvents (the organic layer, which is saturated with water, and the aqueous drug solution) until equilibrium is attained. The content of the drug in one of the layers is determined and the value is calculated. Octanol-water partitioning is the system commonly used for the study. Although the partition coefficient alone may not provide information regarding absorption, it characterizes the lipophilic-hydrophilic balance of a drug and supports the screening of compounds for their biological properties. Combined with LogP, a drugs melting point is also useful for screening compounds for their lipid solubility. Molecules with high melting point tend to be less soluble than predicted from their LogP. Molecules with low melting point tend to be more soluble than predicted from their LogP.

As understood herein, an analgesic agent is any member of the group of drugs used to achieve analgesia, relief from pain. They are distinct from anesthetics, which temporarily affect, and in some instances eliminate, sensation. Examples of suitable analgesics can include a nonsteroidal anti-inflammatory drug (NSAID), a COX-2 inhibitor, or a mixture thereof. Non-limiting examples of NSAIDs can include ibuprofen, naproxen, diclofenac, mefenamic acid, indomethacin, cannabidiol, an ion pair thereof, a salt thereof, or a mixture thereof. Non-limiting examples of COX-2 inhibitors can include etoricoxib, meloxicam, celecoxib, an ion pair thereof, a salt thereof, or a mixture thereof.

As understood herein, an anesthetic agent refers to any agent that produces a local or general loss of sensation, including pain. Anesthetics achieve this effect by acting on the brain or peripheral nervous system to suppress responses to sensory stimulation. The unresponsive state thus induced is known as anesthesia. General anesthesia involves loss of consciousness, usually for the purpose of relieving the pain of surgery. Local anesthesia involves loss of sensation and/or motor function in one area of the body by the blockage of conduction in nerves.

While the instant disclosure describes using local anesthetics, it is possible to include a general anesthetic. Suitable examples of local anesthetics include an ester-based anesthetic, an amide-based anesthetic, or a mixture thereof. Non-limiting examples of ester-based anesthetics include procaine, amethocaine, benzocaine, tetracaine, or a mixture thereof. Non-limiting examples of amide-based anesthetic include lidocaine, prilocaine, bupivacaine, levobupivacaine, ropivacaine, mepivacaine, dibucaine, etidocaine, a salt thereof, or a mixture thereof. The amide-based anesthetics can include the freebase form of the amide-based anesthetic, a hydrochlorinated form of the amide-based anesthetic, or additional salt forms or ion pairs of the amide-based anesthetic including lipophilic salts. A lipophilic salt of the amide-based anesthetic involves pairing the protonated amid-based anesthetic with a lipophilic counterion, which can enhance the solubility of the amide-based anesthetic in the lipophilic oil. This can be beneficial in increasing the loading of the anesthetic agent in the pharmaceutical composition. For example, a lipophilic salt or ion pair of the amide-based anesthetic can include a docusate counterion. As an example, the lipophilic salt or ion pair of the amide-based anesthetic can be ropivacaine docusate. As further examples the amide-based local anesthetic is an ion pair, or salt, comprising of bupivacaine butyrate, bupivacaine palmitate, bupivacaine laureate, bupivacaine myristate, bupivacaine stearate, bupivacaine hydroxystearate, bupivacaine oleate, bupivacaine ricinolate, bupivacaine docusate.

While any of the aforementioned amide-based anesthetics are desirable, ropivacaine can be desirable for use because it includes several known clinical advantages such as good patient safety and good analgesic properties such as sensory selectivity. However ropivacaine typically exhibits poor solubility in lipophilic oils (including but not limited to medium-chain triglycerides). The relatively poor solubility extends to the freebase and hydrochlorinated forms of ropivacaine. However, it has been unexpectedly shown that ropivacaine docusate exhibits suitable solubility in lipophilic oils such as medium-chain triglycerides to allow for a sufficient amount of ropivacaine to be dissolved in the lipophilic oil and to be released at an acceptable rate.

Suitable examples of anti-inflammatory agents can include aspirin, celecoxib, diclofenac, diflunisal, etodolac, ibuprofen, indomethacin, ketoprofen, ketorolac, nabumetone, naproxen, oxaprozin, piroxicam, salsalate, sulindac, tolmetin, or a mixture thereof.

The pharmaceutical composition can include an adjuvant. In the context of drug, an adjuvant refers to drugs with a primary indication other than pain that have analgesic properties. Examples of suitable adjuvants include a barbiturate, an opiate, an anti-inflammatory agent, a cannabinoid, a sympatholytic agent or a mixture thereof. Further examples of suitable adjuvants include corticosteroid, dexamethasone, pethidine, tubocurarine chloride, meloxicam, dexmedetomidine or a mixture thereof.

If the adjuvant includes a cannabinoid, a suitable cannabinoid can be cannabidiol (CBD). However it is possible that other cannabinoids can include cannabigerolic acid (CBGA), cannabigerolic acid monomethylether (CBGAM), cannabigerol (CBG), cannabigerol monomethylether (CBGM), cannabigerovarinic acid (CBGVA), cannabigerovarin (CBGV), cannabichromenic acid (CBCA), cannabichromene (CBC), cannabichromevarinic acid (CBCVA), cannabichromevarin (CBCV), cannabidiolic acid (CBDA), cannabidiol monomethylether (CBDM), cannabidiol-C4 (CBD-C4), cannabidivarinic acid (CBDVA), cannabidivarin (CBDV), cannabidiorcol (CBD-C1), tetrahydrocannabinolic acid A (THCA-A), tetrahydrocannabinolic acid B (THCA-B), tetrahydrocannabinolic acid (THCA), tetrahydrocannabinol (THC), tetrahydrocannabinolic acid C4 (THCA-C4), tetrahydrocannbinol C4 (THC-C4), tetrahydrocannabivarinic acid (THCVA), tetrahydrocannabivarin (THCV), tetrahydrocannabiorcolic acid (THCA-C1), tetrahydrocannabiorcol (THC-C1), Δ7-cis-iso-tetrahydrocannabivarin, Δ8-tetrahydrocannabinolic acid (Δ8-THCA), cannabivarinodiolic (CBNDVA), cannabivarinodiol (CBNDV), Δ8-tetrahydrocannabinol (Δ8-THC), Δ9-tetrahydrocannabinol (Δ9-THC), cannabicyclolic acid (CBLA), cannabicyclol (CBL), cannabicyclovarin (CBLV), cannabielsoic acid A (CBEA-A), cannabielsoic acid B (CBEA-B), cannabielsoin (CBE), cannabivarinselsoin (CBEV), cannabivarinselsoinic acid (CBEVA), cannabielsoic acid (CBEA), cannabielvarinsoin (CBLV), cannabielvarinsoinic acid (CBLVA), cannabinolic acid (CBNA), cannabinol (CBN), cannabivarinic acid (CBNVA), cannabinol methylether (CBNM), cannabinol-C4 (CBN-C4), cannabivarin (CBV), cannabino-C2 (CBN-C2), cannabiorcol (CBN-C1), cannabinodiol (CBND), cannabinodiolic acid (CBNDA), cannabinodivarin (CBDV), cannabitriol (CBT), 10-ethoxy-9-hydroxy-Δ8a-tetrahydrocannabinol, 8,9-dihydroxy-Δ6a(10a)-tetrahydrocannabinol (8,9-Di-OH-CBT-C5), cannabitriolvarin (CBTV), ethoxy-cannabitriolvarin (CBTVE), dehydrocannabifuran (DCBF), cannbifuran (CBF), cannabichromanon (CBCN), cannabicitran (CBT), 10-oxo-Δ6a(10a)-tetrahydrocannabinol (OTHC), Δ9-cis-tetrahydrocannabinol (cis-THC), cannabiripsol (CBR), 3,4,5,6-tetrahydro hydroxy-alpha-alpha-2-trimethyl-9-n-propyl-2,6-methano-2H-1-benzoxocin-5-methanol (OH-iso-HHCV), trihydroxy-delta-9-tetrahydrocannabinol (triOH-THC), yangonin, epigallocatechin gallate, dodeca-2E,4E,8Z,10Z-tetraenoic acid isobutylamide, and dodeca-2E,4E-dienoic acid isobutylamide, a mixture thereof, or a mixture of any of the foregoing with cannabidiol.

Including the adjuvant can provide a synergistic effect in that the amount of the drug that needs to be added to be considered a therapeutically effective amount can be decreased, relative to a comparative pharmaceutical composition differing only by being free of the adjuvant.

In some aspects, the pharmaceutical composition can include a rheological modifier. Where present, the rheological modifier can be present in a range of from about 0.5% (w/v) to about 10% (w/v) of the pharmaceutical composition based on the volume of the lipophilic oil, about 1% (w/v) to about 6% (w/v), about 1.5% (w/v) to about 3% (w/v), less than, equal to, or greater than about 0.5% (w/v), 1, 1.5, 2, 2.5, 3, 3.5, 4, 4.5, 5, 5.5, 6, 6.5, 7, 7.5, 8, 8.5, 9, 9.5, or about 10% (w/v).

In some aspects, the rheological modifier can be a thinning agent that reduces the viscosity of the pharmaceutical composition. In examples, where the pharmaceutical composition is intended to be injected, the thinning agent can be beneficial in that it can enhance the injectability of the pharmaceutical composition by making it less viscous. For example, the thinning agent can at least temporarily disrupt the supramolecular gel. In addition to increasing the injectability of the pharmaceutical composition, at least temporarily disrupting the supramolecular gel can help to enhance the shelf-life stability of the pharmaceutical composition. For example, if the components of the pharmaceutical composition are homogenously distributed with respect to each other the formation of the supramolecular gel can be delayed until deployed in vivo. Examples of suitable thinning agents can include a C2-C12-alcohol. Non-limiting examples of alcohols can include ethanol, benzyl alcohol, or a mixture thereof. A benefit of using ethanol or benzyl alcohol is that once the pharmaceutical composition, including ethanol or benzyl alcohol, is deployed in vivo the ethanol or benzyl alcohol will diffuse in the aqueous environment allowing for the viscosity of the pharmaceutical composition to increase and/or for complete formation of the supramolecular gel to occur.

In other aspects, the rheological modifier can increase the viscosity of the pharmaceutical composition. This can be helpful, for example, if a particular combination of a lipophilic oil and structuring agent interact well together or allow for adequate dispersion and diffusion of a desired drug but together do not provide a composition having adequate viscosity. Including a rheological modifier to increase the viscosity can make the pharmaceutical composition viable.

Pharmaceutical compositions contain an effective amount of a compound as described herein and optionally one or more other therapeutic agents included in a pharmaceutically acceptable carrier. The term "pharmaceutically acceptable carrier" means one or more compatible solid or liquid fillers, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also can be commingled with the compounds, and with each other, in a manner such that there is no interaction which would substantially impair the desired pharmaceutical efficiency.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body to another organ or portion of the body. Each carrier must be "acceptable" in the sense of being compatible with the other ingredients of the composition, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, castor oil, medium chain triglyceride oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions. Pharmaceutical compositions of the present disclosure are non-pyrogenic, i.e., do not induce significant temperature elevations when administered to a patient.

The pharmaceutical composition can be packaged in any suitable manner. For example, the pharmaceutical composition can be packaged in a jar, vessel, or the like such that the pharmaceutical composition can be accessed and manually applied at a desired location. Alternatively, the pharmaceutical composition can be disposed within a dispensing chamber of a syringe. The syringe can have a needle having a size in a range of from about 14 to about 30 gauge, about 21 to about 25 gauge, less than, equal to, or greater than about 14 gauge, 15, 16, 17, 18, 19, 20, 21, 22, 23, 24, 25, 26, 27, 28, 29, or 30 gauge. Alternatively, the pharmaceutical composition can be disposed from the syringe without a needle (e.g., through a cone applicator).

The pharmaceutical composition can be manufactured by a) mixing the lipophilic oil and the analgesic agent, anesthetic agent (or other drug within the scope of the disclosure) under stirring at a temperature above 25° C. to form a first mixture; b) mixing the structuring agent with the first mixture under stirring and heating at a temperature above 25° C. to form a second mixture; and c) cooling the second mixture to form the pharmaceutical composition.

As an example, the pharmaceutical composition can be manufactured by mixing the lipophilic oil and the drug under stirring at a temperature above room temperature (25° C.). to form a first mixture. For example, the temperature can be in a range of from about 50° C. to about 100° C., about 60° C. to about 80° C., less than, equal to, or greater than about 50° C., 55, 60, 65, 70, 75, 80, 85, 90, 95, or 100° C. The structuring agent can be added to the first mixture under stirring and heating at a temperature above room temperature (25° C.) to form a second mixture. For example, the temperature can be in a range of from about 50° C. to about 100° C., about 60° C. to about 80° C., less than, equal to, or greater than about 50° C., 55, 60, 65, 70, 75, 80, 85, 90, 95, or 100° C. The second mixture can then be cooled to form the pharmaceutical composition. Before the second mixture is cooled it can be placed in the jar, vessel, or syringe so that the supramolecular gel forms therein.

The pharmaceutical composition and/or jar, vessel, or syringe can be sterilized at any point during the manufacturing process. However, as a result of the stability of the pharmaceutical composition, sterilization can occur after the pharmaceutical composition is fully formed (e.g., post cooling). Sterilization can occur using any suitable technique such as ultra violet light treatment, e-beam, x-ray, autoclaving, steam sterilization and dry heat sterilization.

In operation, the pharmaceutical composition can be administered to a subject. The pharmaceutical composition can be administered at or proximate to an injury or wound or treatment site. An example of an injury or wound can include a surgical site. The pharmaceutical composition can be administered distal to an injury or wound. For example, the pharmaceutical composition can be administered to a particular location to block a nerve(s) and therefore block pain from the distal injury or wound. In the context of a surgery, the pharmaceutical composition can be applied before a surgery, during the course of surgery (e.g., any time before the incision is closed) or after surgery (e.g., after the incision is closed).

As used herein, the term "kit" refers to a product (e.g. medicament, kit-of-parts) comprising one package or one or more separate packages of:
  (i). A pharmaceutical composition containing an active pharmaceutical ingredient and at least one further active pharmaceutical ingredient and optionally a medical device. The at least one further active pharmaceutical ingredient may be present in said pharmaceutical composition, i.e. the kit may comprise one or more packages, wherein each package comprises one pharmaceutical composition which comprises two or more active pharmaceutical ingredients. The further active pharmaceutical ingredient may also be present in a further pharmaceutical composition, i.e. the kit may comprise separate packages of two or more pharmaceutical compositions, wherein each pharmaceutical composition contain one active pharmaceutical ingredient.
Or
  (ii). A pharmaceutical composition containing an active pharmaceutical ingredient and medical device.

A kit may comprise one package only or may comprise one or more separate packages. For example, the kit may be a product (e.g. medicament) containing two or more vials each containing a defined pharmaceutical composition, wherein each pharmaceutical composition contains at least one active pharmaceutical ingredient. For example, the kit may comprise (i.) a vial containing a defined pharmaceutical composition and (ii). further a tablet, capsule, powder or any other oral dosage form which contains at least one further active pharmaceutical ingredient. The kit may further comprise a package leaflet with instructions for how to administer the pharmaceutical composition and the at least one further active pharmaceutical ingredient.

As used herein, the term "medical device" means any instrument, apparatus, implant, in vitro reagent or similar or related article that is used to diagnose, prevent, or treat a disease of other condition, and does not achieve its purpose through pharmacological action within or on the body.

As used herein, a medical device may be a syringe, an insulin injection system, an insulin infusion system, an insulin pump or an insulin pen injection device. As used herein, a medical device may be mechanically or electro-mechanically driven.

The ingredients in the pharmaceutical composition can be defined as being Generally Recognized as Safe ("GRAS"). A full list of GRAS ingredients can be found in the GRAS Substances (SCOGS) Database maintained by the United States Food and Drug Administration. About 50% to about 100% of the ingredients in the pharmaceutical composition can be classified as being GRAS ingredients, about 75% to about 100%, about 90% to about 100%, less than, equal to, or greater than about 50%, 55, 60, 65, 70, 75, 80, 85, 90, 95, or about 100% of the ingredients in the pharmaceutical composition can be classified as being GRAS ingredients.

EXAMPLES

Various aspects of the present disclosure can be better understood by reference to the following Examples which are offered by way of illustration. The present disclosure is not limited to the Examples given herein.

TABLE 1

| Materials | |
|---|---|
| Material | Supplier |
| Medium-Chain Triglyceride ("MCT") | IOI Oleochemical, Perai, Malaysia |
| Glycerol Monostearate | Alfa Aesar, Ward Hill, MA |
| Tristearin | IOI Oleochemical, Perai, Malaysia |
| Trimyristin | IOI Oleochemical, Perai, Malaysia |
| Tripalmitin | IOI Oleochemical, Perai, Malaysia |
| Trilaurin | Sigma Aldrich, St. Lous, MO |
| Tributyrin | Acros Organics, Carlsbad, CA |
| Bupivacaine freebase | Cayman Chemical, Ann Arbor, MI |
| Sodium docusate | MP Biomedicals, Santa Anna, CA |
| Ropivacaine freebase | Alpha Aesar, Ward Hill, MA |

Fifteen compositions were prepared. Each composition was prepared by heating a medium-chain triglyceride to about 70° C. The drug (bupivacaine freebase, ropivacaine docusate, or ropivacaine freebase) was added to the heated medium-chain triglyceride and stored. Subsequently the structuring agent (trimyristin, tripalmitin, trilaurin, or glycerol monostearate) was added under heat and stirring until it is sufficiently dissolved. The resulting solution was sucked up into a syringe, air bubbles were removed, and the syringe is capped with an air tight seal. As the solution cooled to room temperature (~25° C.), it spontaneously forms the supramolecular gel. The constituents of the fifteen compositions are provided below in Tables 2-16. In Tables 2-16 concentration values of the structuring agents and drugs of individual compositions are represented as the weight relative to the volume of the lipophilic oil (w/v).

TABLE 2

| Composition 1 | | |
|---|---|---|
| Function | Constituent | Concentration |
| Lipophilic Oil | medium-chain triglyceride | — |
| Structuring Agent | glycerol monostearate | 10-20% (w/v) |
| Drug | bupivacaine freebase | 5% (w/v) |

TABLE 3

Composition 2

| Function | Constituent | Concentration |
|---|---|---|
| Lipophilic Oil | medium-chain triglyceride | — |
| Structuring Agent | glycerol distearate | 10-20% (w/v) |
| Drug | bupivacaine freebase | 5% (w/v) |

TABLE 4

Composition 3

| Function | Constituent | Concentration |
|---|---|---|
| Lipophilic Oil | medium-chain triglyceride | — |
| Structuring Agent | trimyristin | 10-20% (w/v) |
| Drug | bupivacaine freebase | 5% (w/v) |

TABLE 5

Composition 4

| Function | Constituent | Concentration |
|---|---|---|
| Lipophilic Oil | medium-chain triglyceride | — |
| Structuring Agent | tripalmitin | 5-20% (w/v) |
| Drug | bupivacaine freebase | 5% (w/v) |

TABLE 6

Composition 5

| Function | Constituent | Concentration |
|---|---|---|
| Lipophilic Oil | medium-chain triglyceride | — |
| Structuring Agent | monolaurin | 10-20% (w/v) |
| Drug | bupivacaine freebase | 5% (w/v) |

TABLE 7

Composition 6

| Function | Constituent | Concentration |
|---|---|---|
| Lipophilic Oil | medium-chain triglyceride | — |
| Structuring Agent | glycerol monostearate | 10-20% (w/v) |
| Drug | ropivacaine docusate | 5% (w/v) |

TABLE 8

Composition 7

| Function | Constituent | Concentration |
|---|---|---|
| Lipophilic Oil | medium-chain triglyceride | — |
| Structuring Agent | glycerol distearate | 10-20% (w/v) |
| Drug | ropivacaine docusate | 5% (w/v) |

TABLE 9

Composition 8

| Function | Constituent | Concentration |
|---|---|---|
| Lipophilic Oil | medium-chain triglyceride | — |
| Structuring Agent | trimyristin | 10-20% (w/v) |
| Drug | ropivacaine docusate | 5% (w/v) |

TABLE 10

Composition 9

| Function | Constituent | Concentration |
|---|---|---|
| Lipophilic Oil | medium-chain triglyceride | — |
| Structuring Agent | tripalmitin | 10-20% (w/v) |
| Drug | ropivacaine docusate | 5% (w/v) |

TABLE 11

Composition 10

| Function | Constituent | Concentration |
|---|---|---|
| Lipophilic Oil | medium-chain triglyceride | — |
| Structuring Agent | monolaurin | 10-20% (w/v) |
| Drug | ropivacaine docusate | 5% (w/v) |

TABLE 12

Composition 11

| Function | Constituent | Concentration |
|---|---|---|
| Lipophilic Oil | medium-chain triglyceride | — |
| Lipophilic Oil | tributyrin | 5-10% (w/v) |
| Structuring Agent | glycerol monostearate | 10-20% (w/v) |
| Drug | ropivacaine freebase | 5% (w/v) |

TABLE 13

Composition 12

| Function | Constituent | Concentration |
|---|---|---|
| Lipophilic Oil | medium-chain triglyceride | — |
| Lipophilic Oil | tributyrin | 5-10% (w/v) |
| Structuring Agent | glyceryl distearate | 10-15% (w/v) |
| Drug | ropivacaine freebase | 5% (w/v) |

TABLE 14

Composition 13

| Function | Constituent | Concentration |
|---|---|---|
| Lipophilic Oil | medium-chain triglyceride | — |
| Lipophilic Oil | tributyrin | 5-10% (w/v) |
| Structuring Agent | trimyristin | 10-20% (w/v) |
| Drug | ropivacaine freebase | 5% (w/v) |

TABLE 15

Composition 14

| Function | Constituent | Concentration |
| --- | --- | --- |
| Lipophilic Oil | medium-chain triglyceride | — |
| Lipophilic Oil | tributyrin | 5-10% (w/v) |
| Structuring Agent | tripalmitin | 10-25% (w/v) |
| Drug | ropivacaine freebase | 5% (w/v) |

TABLE 16

Composition 15

| Function | Constituent | Concentration |
| --- | --- | --- |
| Lipophilic Oil | medium-chain triglyceride | — |
| Lipophilic Oil | tributyrin | 5-10% (w/v) |
| Structuring Agent | trilaurin | 10-15% (w/v) |
| Drug | ropivacaine freebase | 5% (w/v) |

TABLE 17

Composition 15

| Function | Constituent | Concentration |
| --- | --- | --- |
| Lipophilic Oil | medium-chain triglyceride | — |
| Lipophilic Oil | Castor oil | 10-50% (w/v) |
| Structuring Agent | tristearin | 3-15% (w/v) |
| Drug | bupivacaine freebase | 5% (w/v) |

TABLE 18

Composition 15

| Function | Constituent | Concentration |
| --- | --- | --- |
| Lipophilic Oil | medium-chain triglyceride | — |
| Lipophilic Oil | Castor oil | 10-50% (w/v) |
| Structuring Agent | tripalmitin | 10-15% (w/v) |
| Drug | bupivacaine freebase | 5% (w/v) |

TABLE 19

Composition 15

| Function | Constituent | Concentration |
| --- | --- | --- |
| Lipophilic Oil | medium-chain triglyceride | — |
| Lipophilic Oil | Castor oil | 10-50% (w/v) |
| Structuring Agent | tristearin | 3-15% (w/v) |
| Drug | bupivacaine oleic acid | 5% (w/v) |

Example 2

A MCT only formulation including bupivacaine free base and MCT oil and an oleogel formulation including bupivacaine free base, MCT oil (lipophilic oil) and glyceryl monostearate (structuring agent) were studied for their ability to release bupivacaine free base over time. As shown in FIG. 1, the release of bupivacaine free base is slower in the oleogel formulation.

The controlled release of the formulation was evaluated where 0.5 mL of the formulation was placed into a dialysis bag (10 kDa) and submerged in 50 mL sink of phosphate buffered saline (1×; pH 7.4). The samples were placed into a rotating incubator (1 Hz) at 37° C. At designated timepoints, 2 mL of saline was removed and analyzed using ultraviolet visible spectrophotometry (272 nm). The entire sink medium was replaced at each timepoint until drug no longer eluted out of the system.

Example 3

An oleogel formulation including bupivacaine free base, MCT oil and glyceryl monostearate (structuring agent) as well as an oleogel formulation including bupivacaine free base, a lipophilic oil mixture consisting of 75 wt % MCT oil and 25 wt % castor oil, and glyceryl monostearate (structuring agent) were studied for their drug release over time.

Figure 2:
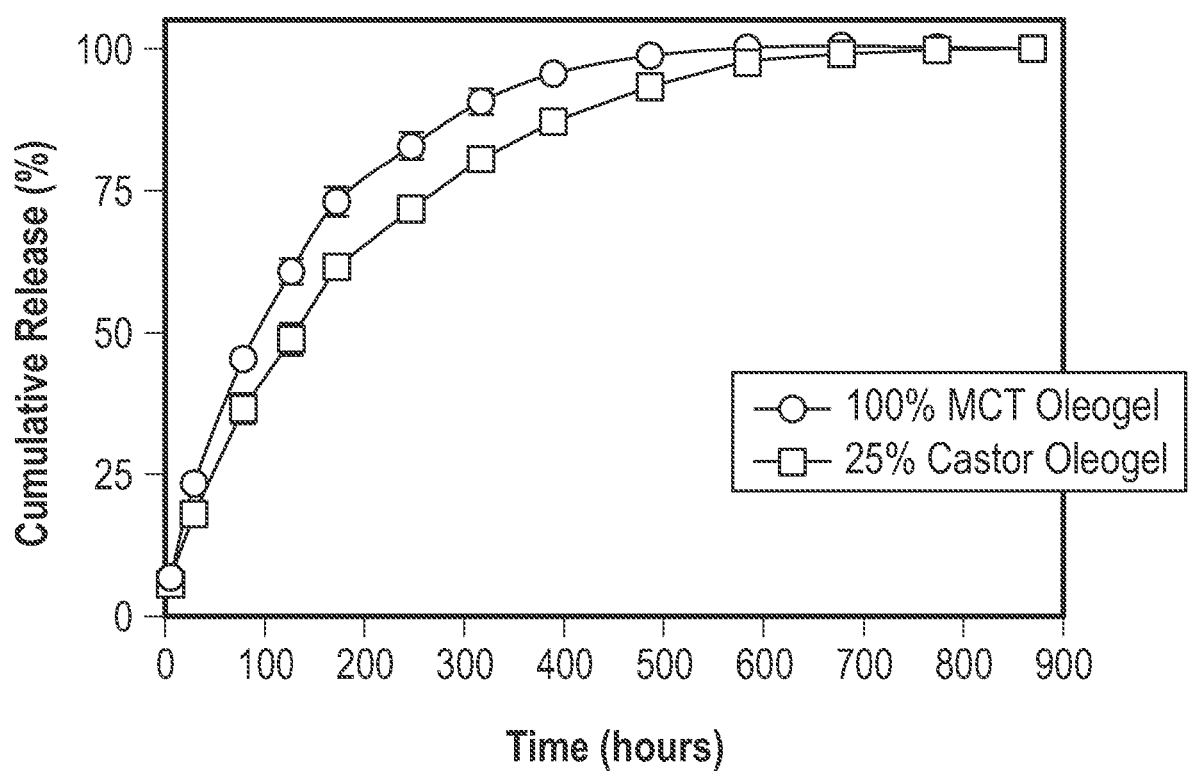
FIG. 2 is a graph showing drug release profiles of various oils.

As shown in FIG. 2, the release of bupivacaine free base is slower in the formulation including the mixture of 75 wt % MCT oil and 25 wt % of castor oil. The drug release profile was measured according to the protocol of Example 2.

Example 4

Figure 3:
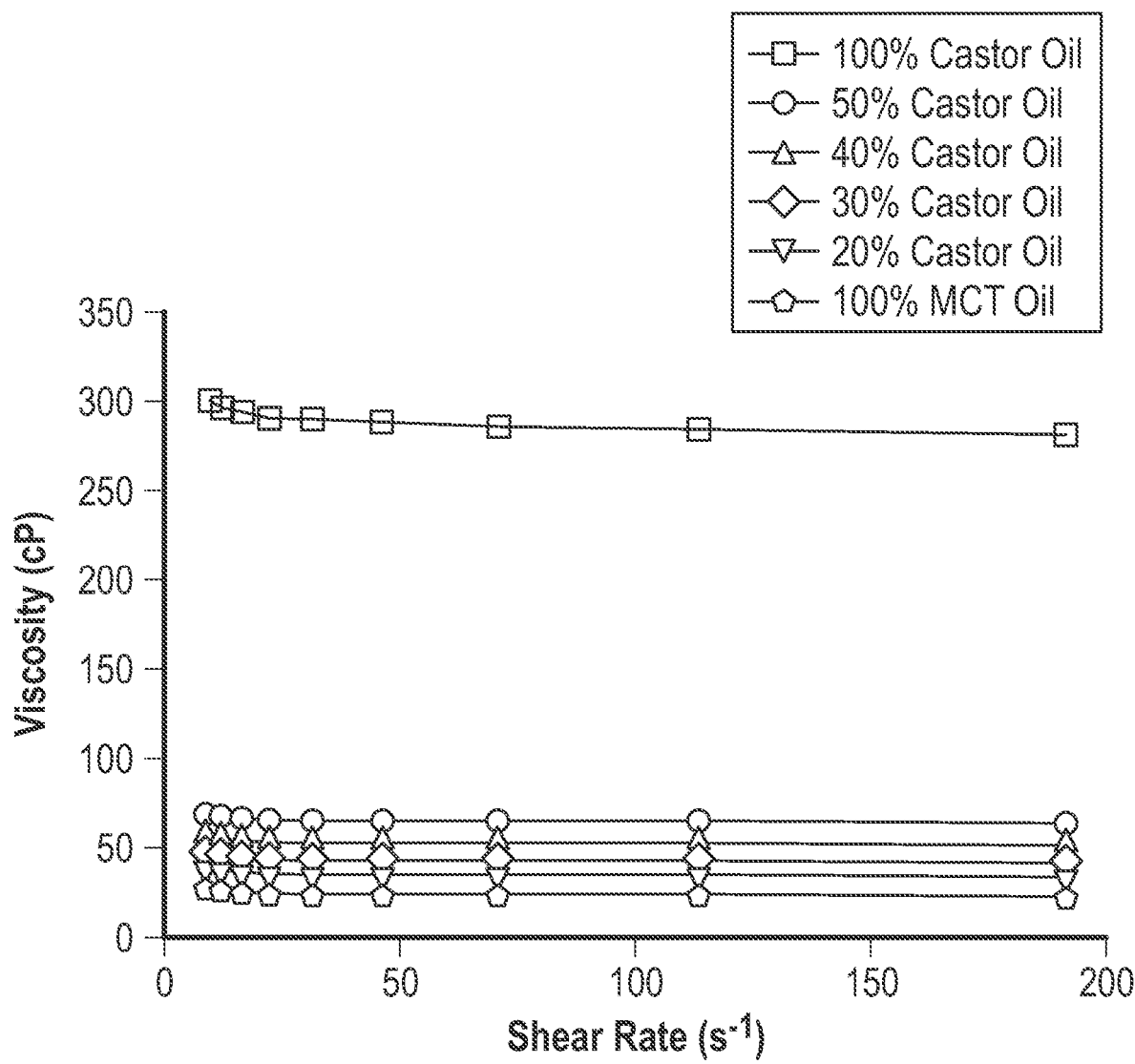
FIG. 3 is a graph showing the viscosity of various oils.

The viscosity of various oils used in the formulations described herein were studied at 37° C. The oils studied included castor oil, MCT oil, and blends of both castor oil and MCT oil (e.g., 50%, 40%, 30%, and 20% castor oil with the balance being MCT). As shown in FIG. 3, blends of MCT: castor, have viscosities that are significantly lower than castor oil alone, and are closer to viscosity values of MCT alone. Given that bupivacaine and other local anesthetics have higher drug solubility in castor oil than MCT, blending the two oils enables both good drug solubility (and thus, drug loading capacity) and low viscosity suitable for injection. For example, these properties mean that 30%-50% castor oil can be included to get higher drug loading and slower drug release without significantly changing the base viscosity of the oil.

A rheometer was used to measure the rheological properties of each formulation. Using a 35 mm parallel plate set up with a 0.5 mm gap, approximately 0.5 mL of the formulation was injected through an 18 G needle onto the rheometer plate for analysis. A rotational ramp test was conducted, at 20° C., and ramped between shear rates of 1-200 Hz to obtain viscosity curves.

Example 5

Figure 4:
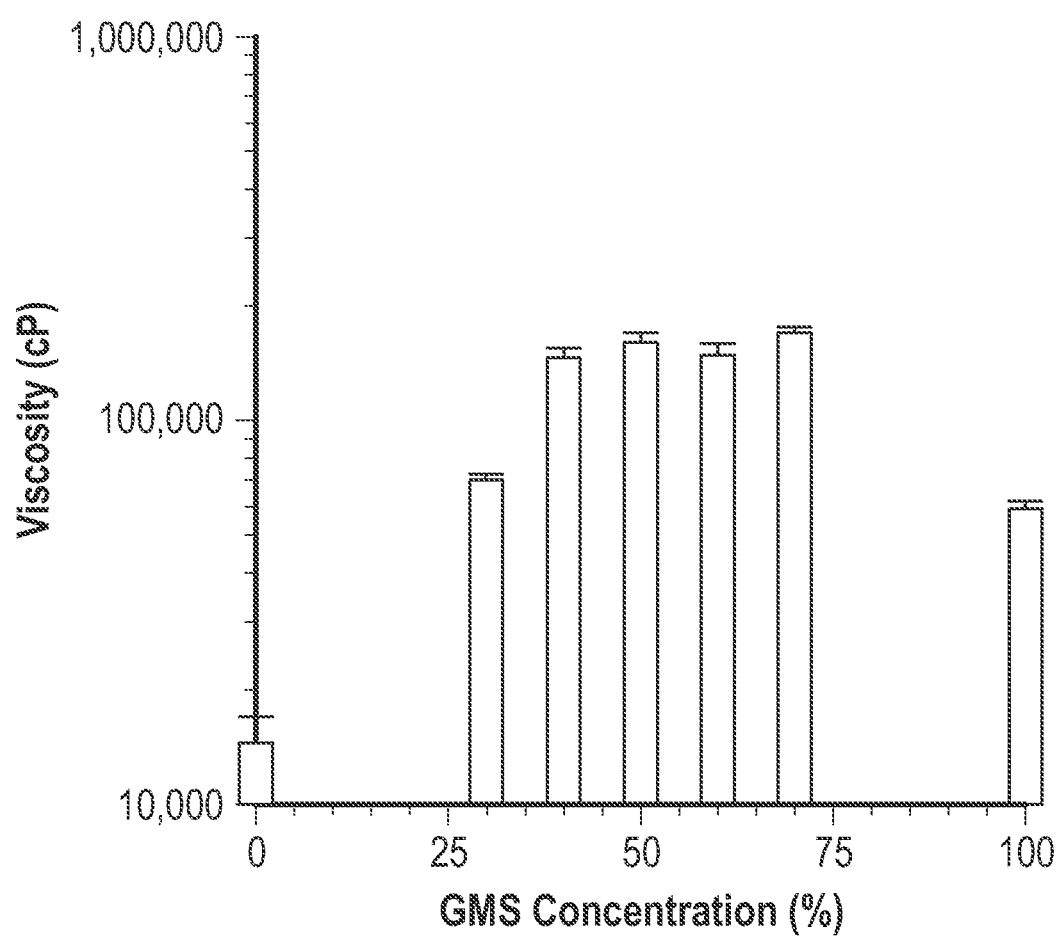
FIG. 4 is a graph showing the effect of varying oil components on viscosity.

The viscosity of a formulation including 25 wt % castor oil and a 20 wt % of a structuring agent was measured at 37° C. The structuring agent included monostearate, monopalmitate and blends thereof. FIG. 4 shows the effect of viscosity with varying the wt % of monostearate in a monostearate and monopalmitate mixture. As shown, formulations with just monostearate or just monopalmitate are significantly weaker than gels made with a blend of the two. Viscosity was measured according to the protocols of Example 4.

Example 6

Figure 5:
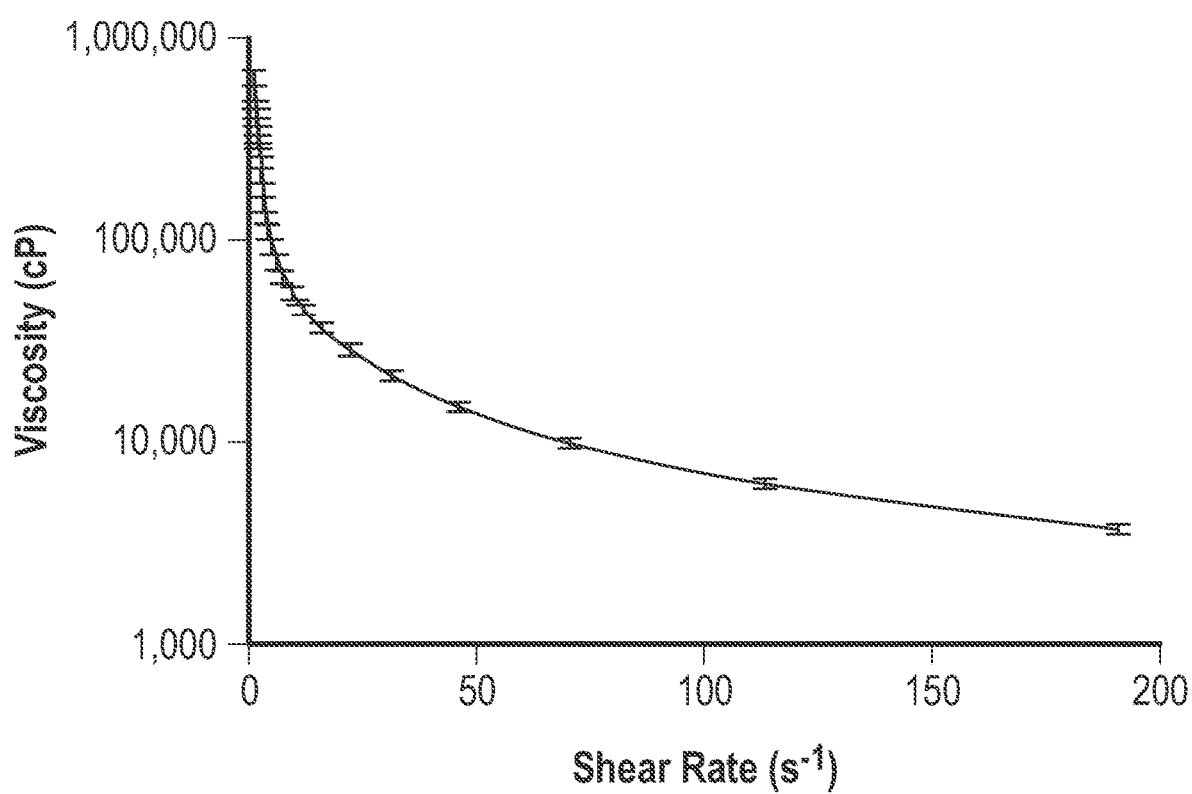
FIG. 5 is a graph showing a viscosity curve of various formulations.

A shear rate of a formulation including 25% monostearate & monopalmitate, 100% MCT, 5% bupivacaine was studied. As shown in FIG. 5, the viscosity curve shows that as shear rate is increased, viscosity lowers. This property can be called "shear thinning" which means that the formulation improves injectability and creates in situ gelling. Viscosity was measured according to the protocols of Example 4.

Example 7

Figure 6:
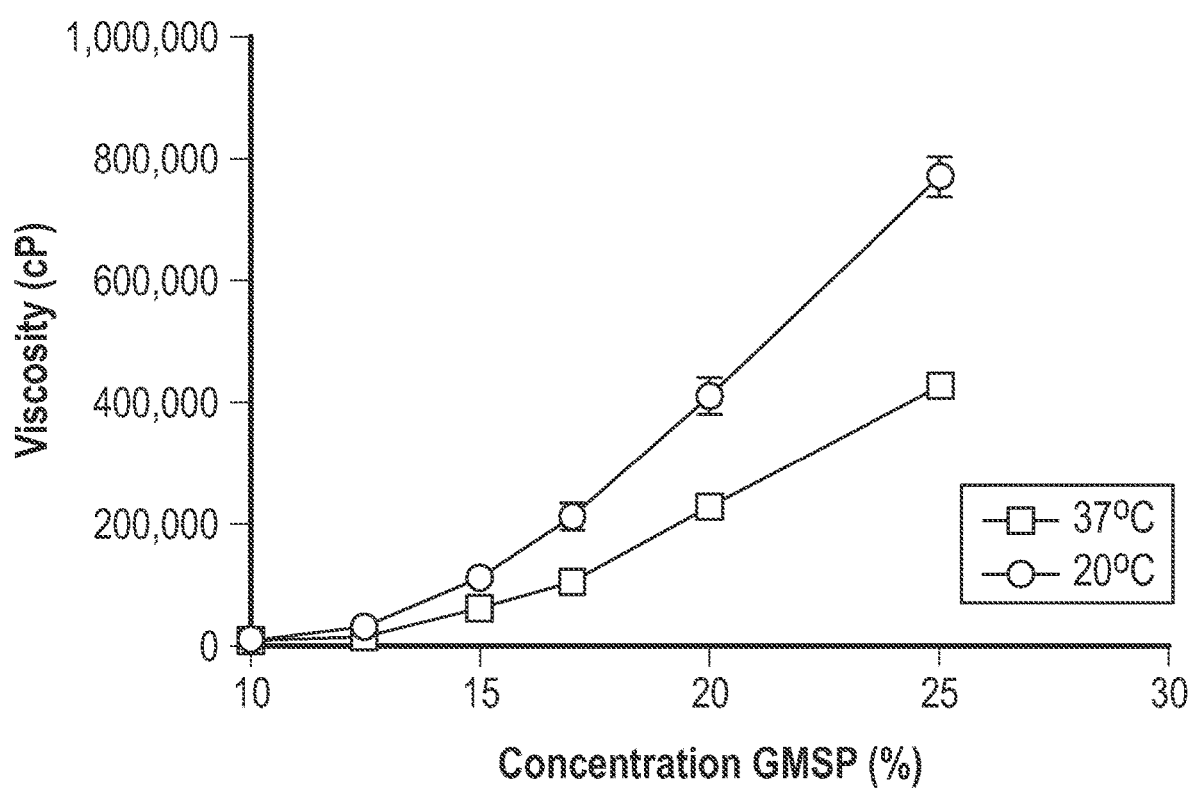
FIG. 6 is a graph showing the viscosity of a formulation at body temperature.
Figure 7A:
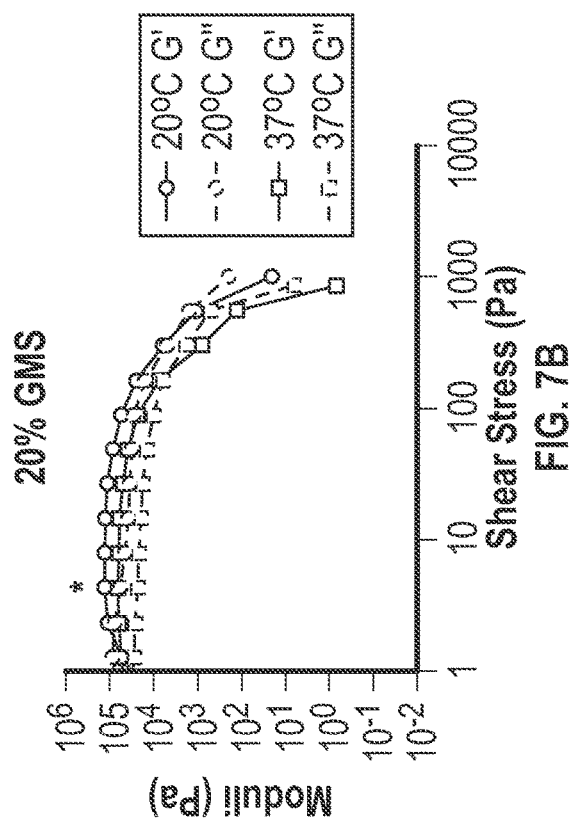
FIGS. 7A-7D are a series of graphs showing storage modulus values of various formulations.
Figure 7B:
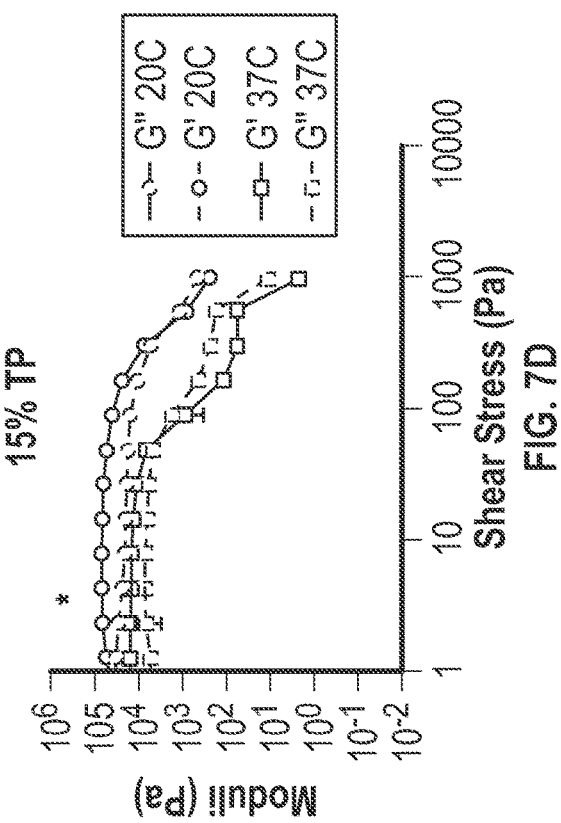
Figure 7C:
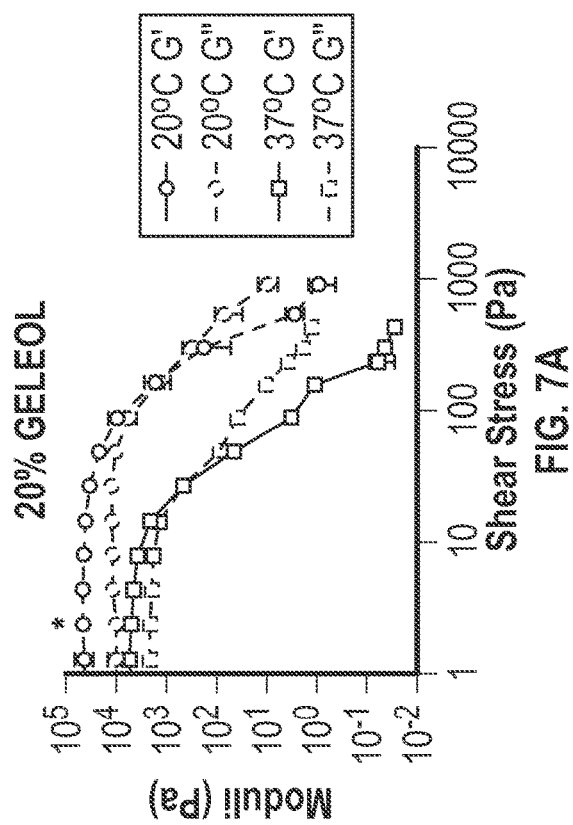
Figure 7D:
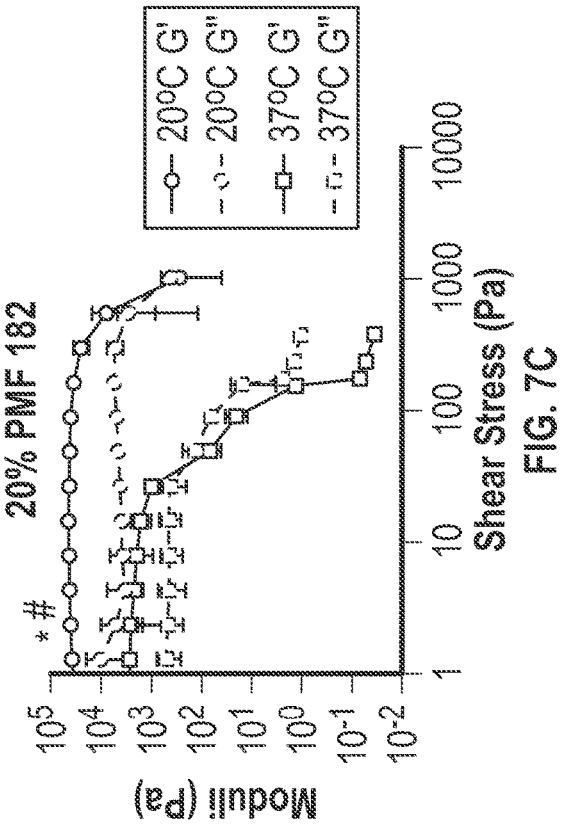

A viscosity of a formulation including MCT a 60:40 monostearate:monpalmitate mixture ("GMSP") and bupivacaine free base was measured at 20° C. and 37° C. (to mimic body temperatures). As shown in FIG. 6, sufficiently strong gels can be obtained. Viscosity was measured according to the protocols of Example 4.

Example 8

Rheology graphs are shown here using different structuring agents. FIGS. 7A-7D show how some of the formulations weaken significantly at 37° C. If a gel falls apart when put at 37° C., it becomes less useful as an injectable depot sustained release drug delivery system. Viscosity was measured according to the protocols of Example 4. The average storage modulus (G'), in the linear viscoelastic region, and crossover point were then obtained from software and further analyzed.

Example 9

DSC melting and crystallization temperatures are shown in Tables 20 and 21, respectively. As shown GMS has melting and crystallization peaks above 37° C. The highest ones out of all the gelators in the previous rheology graphs (FIGS. 7A-7D). Supporting the above results. GMSP gels are more thermostable, making them more useful.

TABLE 20

| Oleogel | 1-Day | | 90-Days | |
| --- | --- | --- | --- | --- |
| | Peak Temperature | Peak Area (AUC) | Peak Temperature | Peak Area (AUC) |
| 15% GELEOL | 46.9° C. ± 0.4° C. | 21.2 J/g ± 1.1 J/g | 48.1° C. ± 1.3° C. | 18.8 J/g ± 0.3 J/g |
| 20% GELEOL | 48.3° C. ± 0.4° C. | 28.4 J/g ± 0.6 J/g | 50.6° C. ± 0.1° C. | 26.7 J/g ± 0.7 J/g |
| 15% GMS | 59.8° C. ± 1.3° C. | 19.2 J/g ± 2.3 J/g | 60.7° C. ± 0.4° C. | 26.5 J/g ± 1.2 J/g |
| 20% GMS | 62.3° C. ± 0.1° C. | 23.4 J/g ± 7.3 J/g | 62.6° C. ± 0.2° C. | 33.2 J/g ± 0.6 J/g |
| 15% PMF | 43.9° C. ± 4.5° C. | 8.6 J/g ± 0.1 J/g | 46.3° C. ± 1.0° C. | 12.8 J/g ± 1.0 J/g |
| 20% PMF | 47.5° C. ± 1.3° C. | 10.9 J/g ± 0.3 J/g | 48.7° C. ± 0.6° C. | 17.1 J/g ± 1.5 J/g |
| 15% TM | 45.4° C. ± 0.2° C. | 19.5 J/g ± 0.1 J/g | 45.5° C. ± 0.1° C. | 21.3 J/g ± 1.2 J/g |
| 20% TM | 47.6° C. ± 0.3° C. | 26.6 J/g ± 0.4 J/g | 47.4° C. ± 0.3° C. | 31.5 J/g ± 1.5 J/g |
| 10% TP | 52.1° C. ± 0.1° C. | 6.4 J/g ± 0.02 J/g | 52.4° C. ± 0.3° C. | 16.6 J/g ± 1.5 J/g |
| 15% TP | 53.9° C. ± 0.6° C. | 8.6 J/g ± 0.7 J/g | 54.5° C. ± 0.1° C. | 22.5 J/g ± 1.2 J/g |

TABLE 21

| Oleogel | 1-Day | | 90-Days | |
| --- | --- | --- | --- | --- |
| | Peak Temperature | Peak Area (AUC) | Peak Temperature | Peak Area (AUC) |
| 15% GELEOL | 29.4° C. ± 0.4° C. | −18.4 J/g ± 0.7 J/g | 28.8° C. ± 0.0° C. | −12.1 J/g ± 2.9 J/g |
| 20% GELEOL | 31.8° C. ± 0.2° C. | −18.4 J/g ± 0.5 J/g | 35.1° C. ± 0.0° C. | −16.5 J/g ± 1.7 J/g |
| 15% GMS | 37.9° C. ± 1.1° C. | −9.8 J/g ± 1.5 J/g | 40° C. ± 0.3° C. | −12.0 J/g ± 0.5 J/g |
| 20% GMS | 42.3° C. ± 0.3° C. | −11.4 J/g ± 2.8 J/g | 42.8° C. ± 0.2° C. | −15.3 J/g ± 0.6 J/g |
| 15% PMF | 33.2° C. ± 3.3° C. | −9.9 J/g ± 0.4 J/g | 38.2° C. ± 0.8° C. | −11.2 J/g ± 0.9 J/g |
| 20% PMF | 37.0° C. ± 0.5° C. | −12.1 J/g ± 1.8 J/g | 40.1° C. ± 0.3° C. | −16.0 J/g ± 0.6 J/g |
| 15% TM | 2.6° C. ± 0.5° C. | −19.7 J/g ± 0.9 J/g | 1.85° C. ± 0.4° C. | −18.6 J/g ± 0.0 J/g |
| 20% TM | 4.7° C. ± 0.3° C. | −22.3 J/g ± 0.9 J/g | 4.75° C. ± 0.4° C. | −26.4 J/g ± 0.1 J/g |
| 10% TP* | 14.2° C. ± 0.3° C. | −6.0 J/g ± 0.01 J/g | 13.5° C. ± 0.3° C. | −14.8 J/g ± 1.0 J/g |
| 15% TP* | 15.9° C. ± 0.5° C. | −8.2 J/g ± 0.7 J/g | 15.9° C. ± 0.1° C. | −20.4 J/g ± 0.8 J/g |

In Tables 20 and 21:
GMS—glyceryl monostearate
PMF=polyglyceride ester of a fatty acid (18C length fatty acids)
TM=trimyristin
TP—tripalmitin Example 10

Figure 8B:
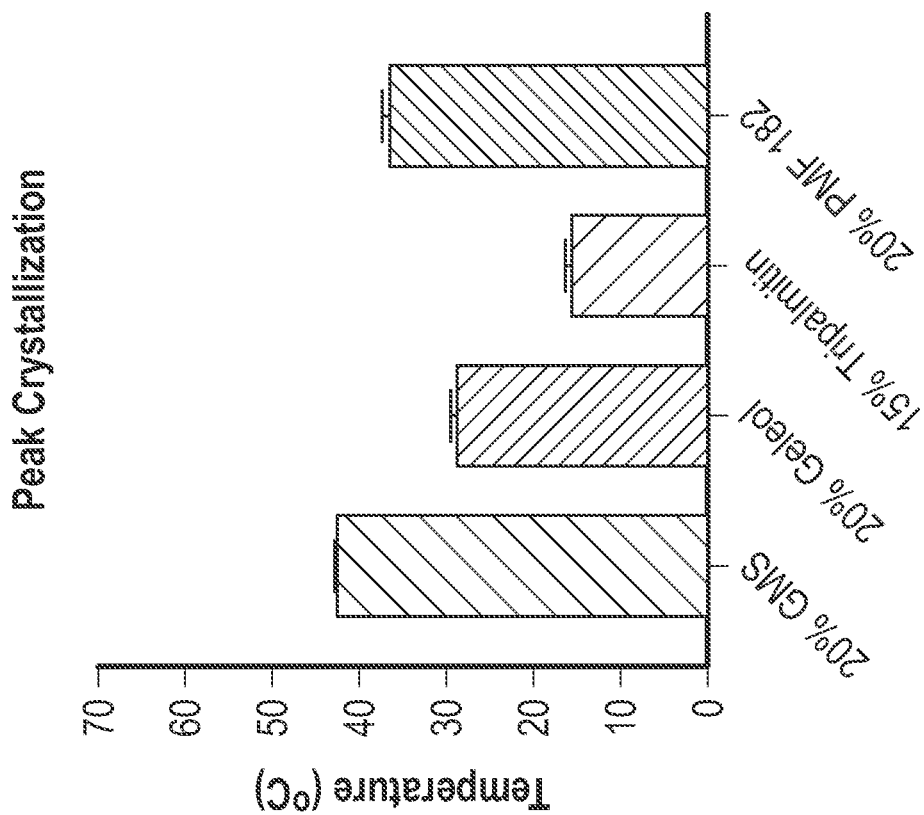
FIGS. 8A and 8B are graphs showing peak melting and peak crystallization properties of various formulations.
Figure 8A:
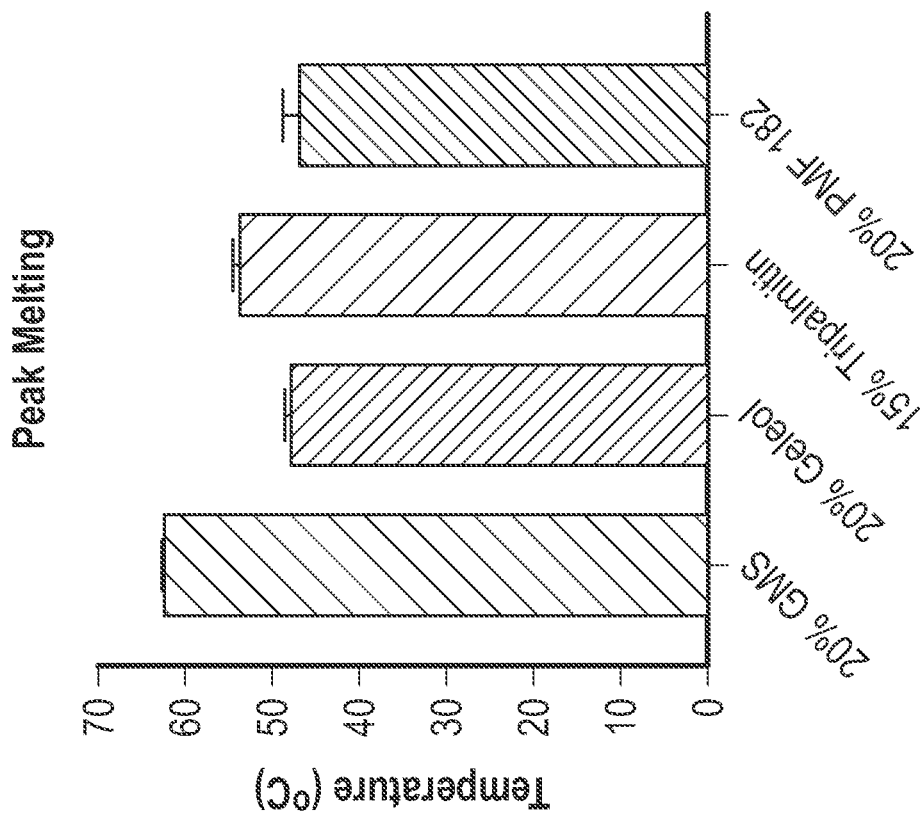

FIGS. 8A and 8B show peak melting and peak crystallization properties of various formulations. The thermal properties of oleogels (e.g., lipophilic oil and structuring agent) were determined using differential scanning calorimetry (DSC). Approximately 25 mg of oleogel was loaded into standard aluminum crucibles (25 µL) with a center pierced lid at room temperature. With a scanning rate of 10° C./min, samples were heated from 20° C. to 100° C. then subsequently cooled to −20° C. after a 5-minute isothermal hold at 100° C.

The area under the curve, or enthalpy of melting, and peak temperatures were obtained using this method.

Example 11

Figure 9A:
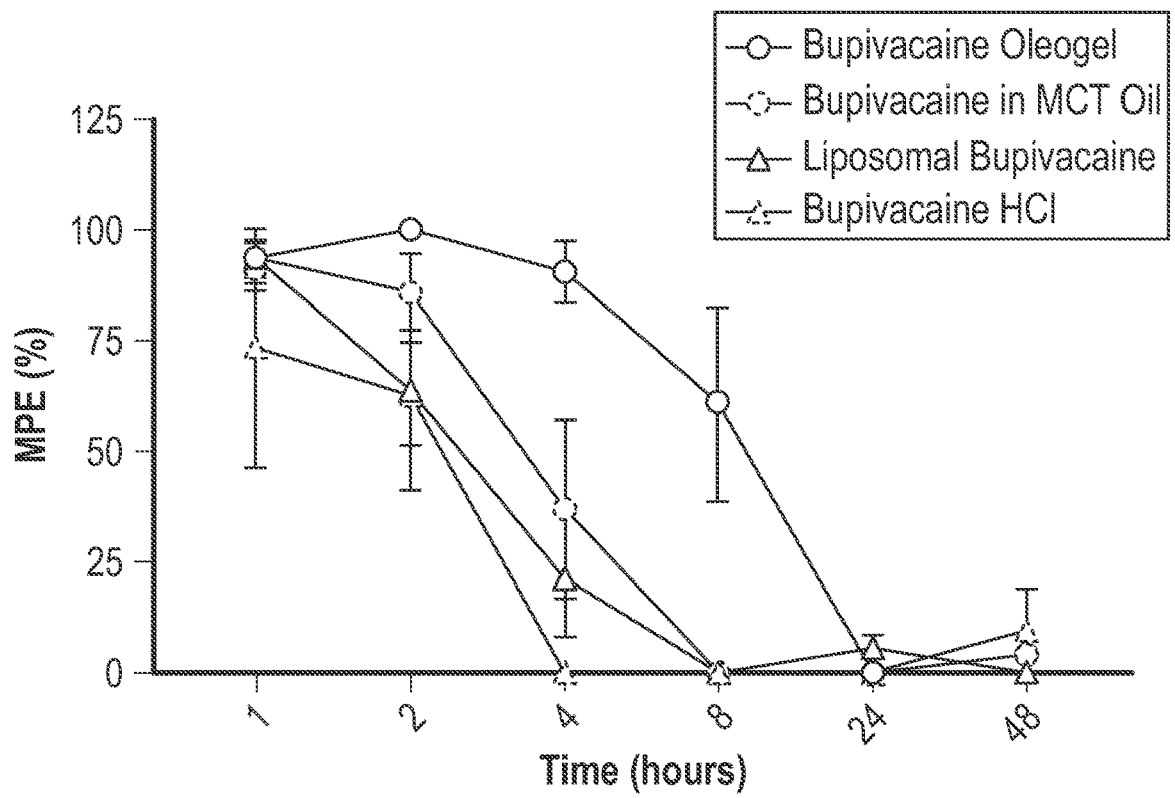
FIGS. 9A and 9B are graphs showing rat sciatic nerve block data for various formulations.
Figure 9B:
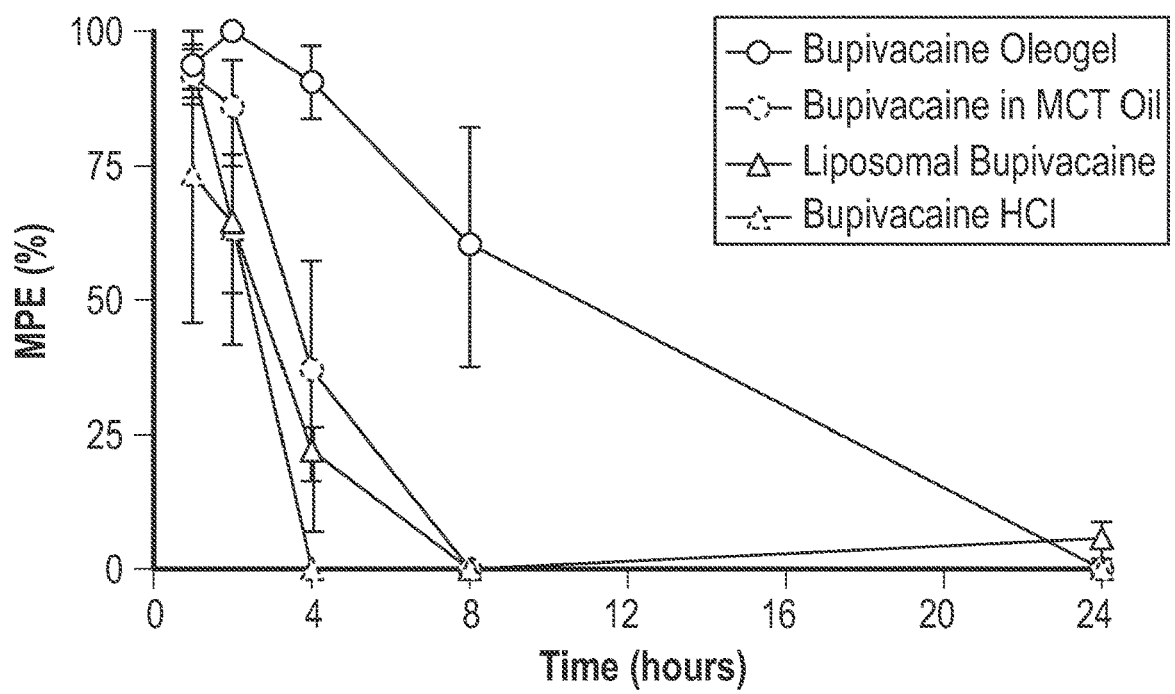

FIGS. 9A and 9B show rat sciatic nerve block data. FIG. 9B shows the same data as FIG. 9A but with different y-axis and x-axis values. As shown bupivacaine in oleogel has the longest effect. More importantly, the oleogel has a longer effect than the MCT oil without the structuring agent, and they both have the same dose of bupivacaine. By turning the oil into a gel, the drug release in vivo is greatly prolonged.

This longitudinal experiment where seventeen male CD Sprague Dawley rats, weighing between 360 and 420 grams underwent a sciatic nerve block with one of four different treatments: 0.3 mL of 0.5% bupivacaine HCl (1.5 mg bupivacaine), 0.3 mL of 1.33% liposomal bupivacaine (4 mg bupivacaine), 0.2 mL of 5% bupivacaine in MCT oil (10 mg bupivacaine), or 0.2 mL of 5% bupivacaine oleogel (w/v) (bupivacaine/oleogel) using 20% GMS (w/v) (GMS/MCT) (10 mg bupivacaine). Each group contained 5 animals with the exception of 0.5% bupivacaine HCl which contained 2 animals as the anesthetic effect of bupivacaine HCl is already well understood. Once the animals had recovered from surgery, they were moved into independent acrylic enclosures on a heated clear glass surface to undergo the Hargreaves pain assay.

Method for Hargreaves: At designated timepoints, a noxious thermal was placed on the mid-plantar portion of the right hind-paw and was turned off manually when the paw was withdrawn. Paw withdrawal latencies were measured three times per timepoint per animal and averaged.

Example 12

Figure 10:
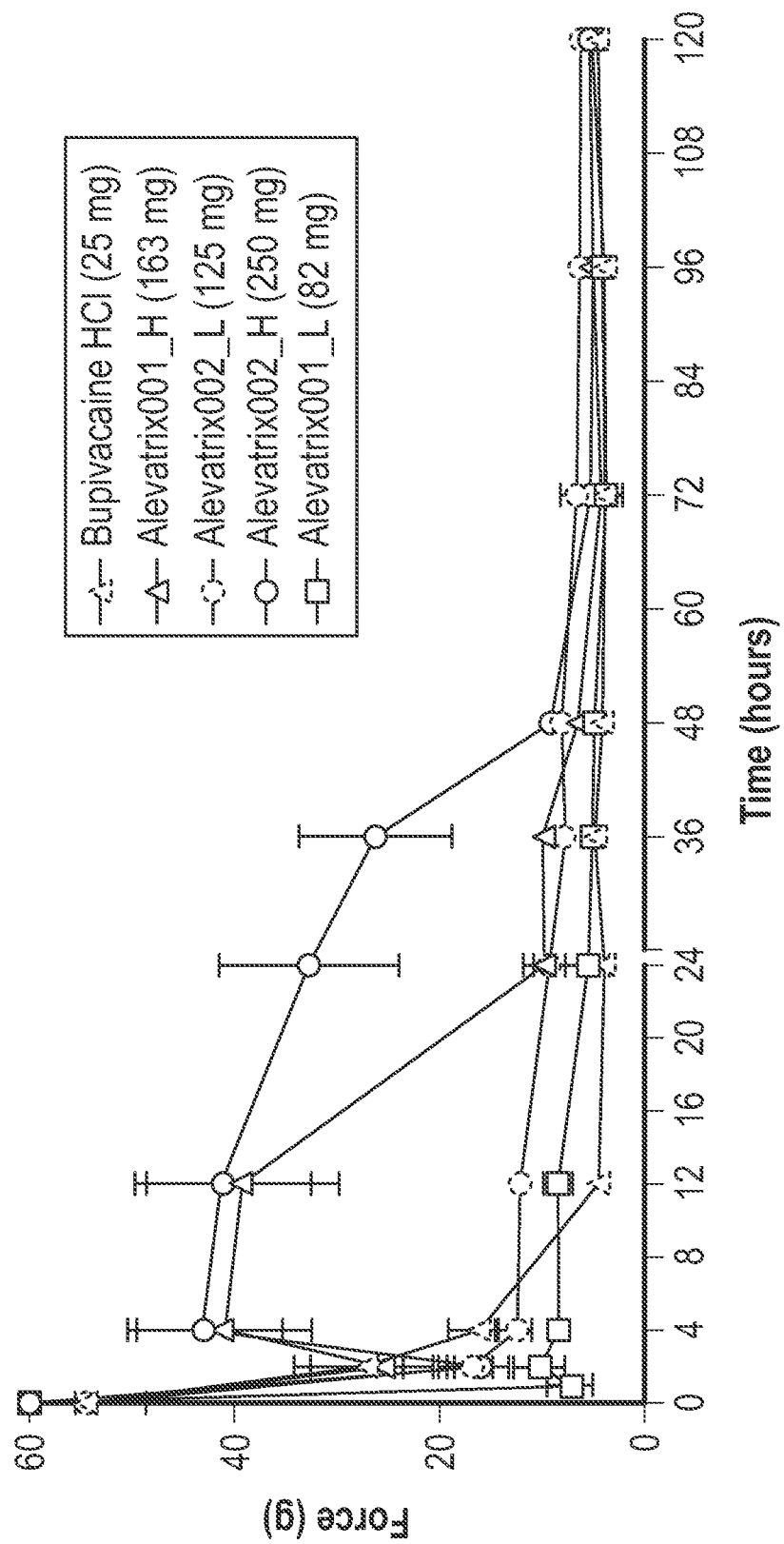
FIG. 10 is a graph showing efficacy data of various formulations in a pig incisional wound model.

FIG. 10 is a graph showing Pig efficacy data. Alevatrix 001=100% MCT. Alevatrix002=75:25 MCT: castor oil. The 002 castor blend group showed a better release profile of bupivacaine Thirty pigs, weighing between 10-13 kg, underwent a subcutaneous injection of each formulation. At designated timepoints the von Frey method was conducted approximately 0.5 cm from the injection site. Where, filaments of increasing diameter were applied in ascending order until a withdrawal reaction was observed, where a filament of 60-gram force is the maximum. Withdrawal reaction was considered as an act of moving away from the stimuli—either by walking away or by twisting the flank. After surgery, pain (allodynia) was considered present if flank withdrawal force was <8 g.

Treatment groups (n=6); low doses (L) had administered volume of 2.5 mL. High doses (H) had an administered volume of 5 mL.

Example 13

Figure 11:
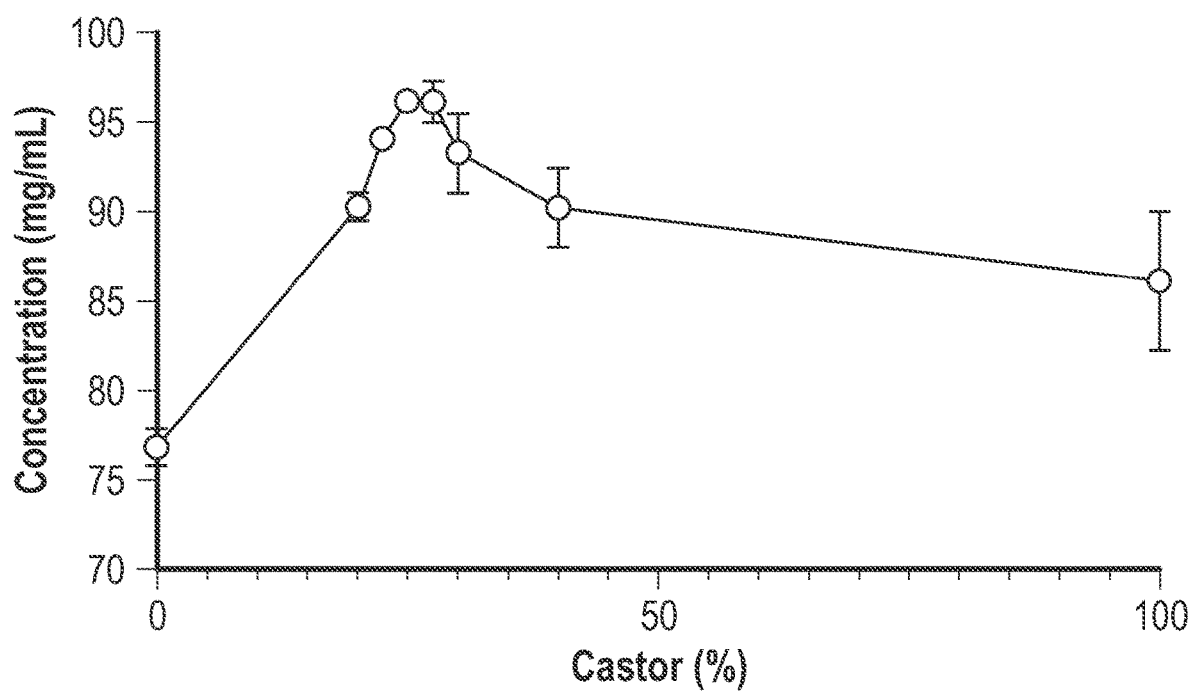
FIG. 11 is a graph showing the solubility of bupivacaine in various blends of MCT oil and castor oil.

The solubility of bupivacaine in a blend of MCT oil and castor oil was studied. As shown in FIG. 11, drug loading increases with specific blends of oil, drug release also slows, because of greater drug affinity to the oil blend. Greater drug affinity higher drug loading and slower release. The max solubility of the oil blends was determined by adding 300 mg of bupivacaine free base into 3 mL of an MCT: castor oil mixture. The mixtures were allowed to rotate on a nutating shaker in an oven at 37° C. overnight to allow for full solubility. After rotating, samples were spun in a centrifuge at 2000×g for 5 minutes. Next, 30 uL of sample supernatant was taken and dissolved to 1470 uL of ethanol and analyzed using ultraviolet visible spectrophotometry (272 nm).

Example 14

Figure 12:
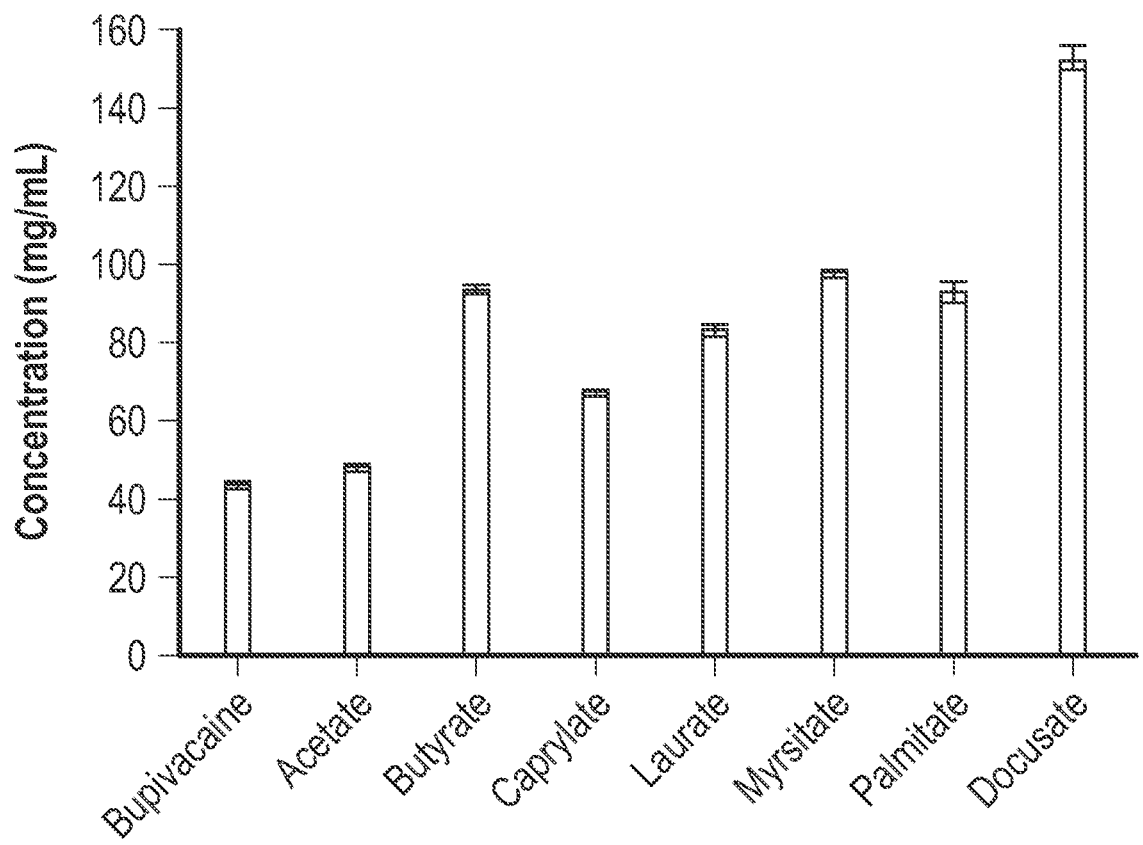
FIG. 12 is a graph showing the solubility of bupivacaine and various lipophilic salts of bupivacaine in MCT oil.

The solubility of bupivacaine is shown in a formulation including MCT oil and glycerol monostearate as a structuring agent with and without the presence of an anion (shown in the x-axis of FIG. 12) is shown in in FIG. 12. As shown docusate increases the solubility of bupivacaine. The solubility was determined according to the protocol of Example 13.

Example 15

Figure 13:
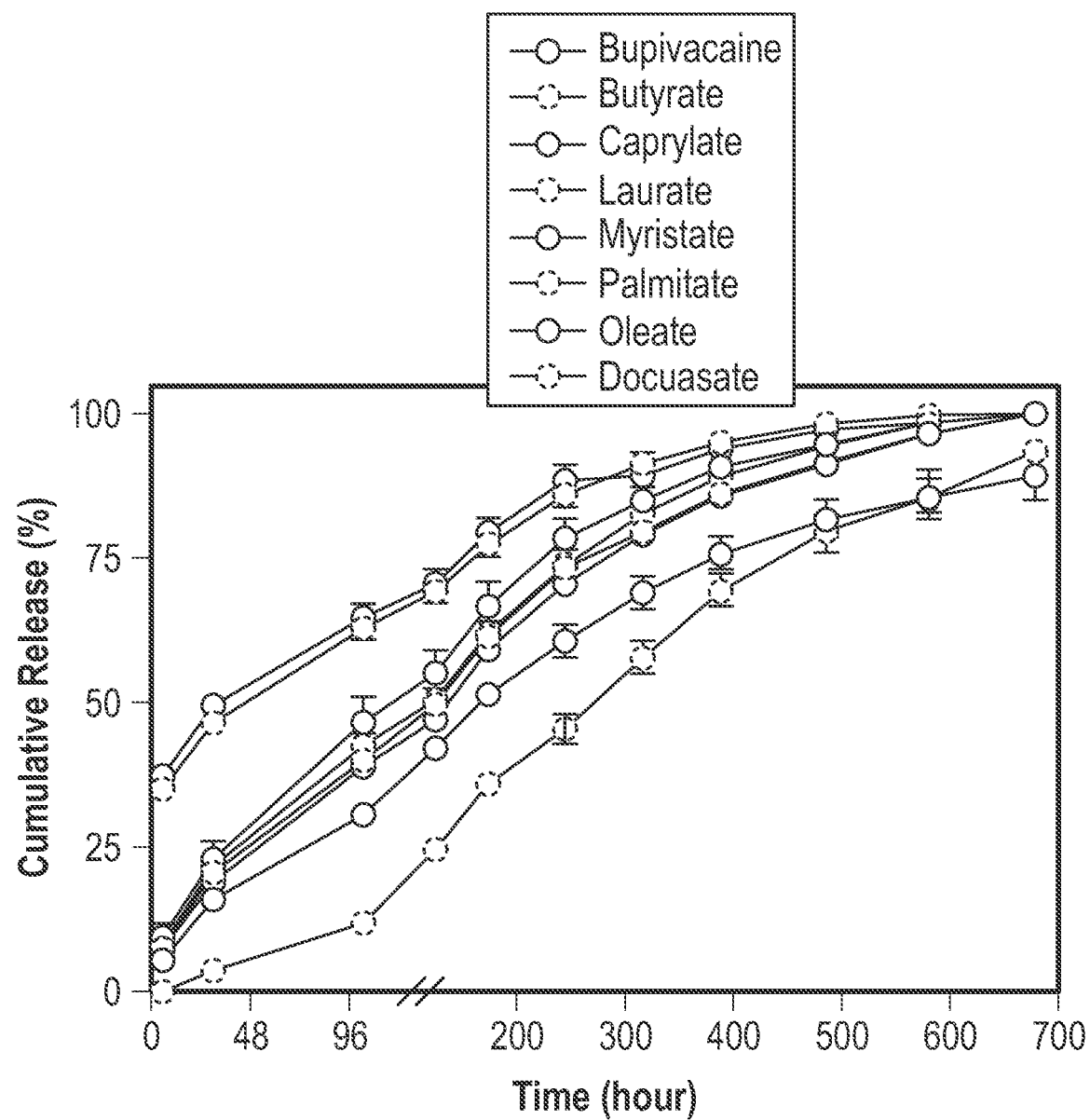
FIG. 13 is a graph showing the release properties of bupivacaine and various lipophilic salts of bupivacaine in MCT oil.

The release of bupivacaine is shown in a formulation including MCT oil and glycerol monostearate as a structuring agent with and without the presence of an anion to increase hydrophobicity. As shown in FIG. 13, the release of bupivacaine with docusate is prolonged. The controlled release of the formulation was evaluated where 0.5 mL of the formulation was placed into a dialysis bag (10 kDa) and submerged in 50 mL sink of phosphate buffered saline (lx; pH 7.4). The samples were placed into a rotating incubator (1 Hz) at 37° C. At designated timepoints, 2 mL of saline was removed and analyzed using ultraviolet visible spectrophotometry (272 nm). The entire sink medium was replaced at each timepoint until drug no longer eluted out of the system.

The terms and expressions that have been employed are used as terms of description and not of limitation, and there is no intention in the use of such terms and expressions of excluding any equivalents of the features shown and described or portions thereof, but it is recognized that various modifications are possible within the scope of the aspects of the present disclosure. Thus, it should be understood that although the present disclosure has been specifically disclosed by specific aspects and optional features, modification and variation of the concepts herein disclosed may be resorted to by those of ordinary skill in the art, and that such modifications and variations are considered to be within the scope of aspects of the present disclosure.

Exemplary Aspects.

The following exemplary aspects are provided, the numbering of which is not to be construed as designating levels of importance:

Aspect 1 provides a pharmaceutical composition, comprising:
a lipophilic oil;
a therapeutic agent, salt, ion pair thereof, or prodrug thereof dispersed in the lipophilic oil; and
a structuring agent at least a portion of which is not dissolved in the lipophilic oil and forms a gel.

Aspect 2 provides the pharmaceutical composition of Aspect 1, wherein the lipophilic oil comprises a monoglyceride, diglyceride, triglyceride, medium-chain triglyceride oil, sesame oil, soybean oil, castor oil, vegetable oil, tributyrin oil, or a mixture thereof.

Aspect 3 provides the pharmaceutical composition of Aspect 2, wherein the triglyceride is a saturated triglyceride, a monounsaturated triglyceride, or a polyunsaturated triglyceride.

Aspect 4 provides the pharmaceutical composition of Aspect 2, wherein the triglyceride comprises a medium-chain triglyceride, a short-chain triglyceride, long-chain triglyceride, or a mixture thereof.

Aspect 5 provides the pharmaceutical composition of Aspect 4, wherein the triglyceride comprises the medium-chain triglyceride.

Aspect 6 provides the pharmaceutical composition of Aspect 5, wherein the medium-chain triglyceride comprises a glyceride of a C6-C12 carboxylic acid, or a mixture thereof.

Aspect 7 provides the pharmaceutical composition of Aspect 1, wherein the structuring agent has a melting point in a range of from about 40° C. to about 100° C.

Aspect 8 provides the pharmaceutical composition of Aspect 7, wherein the structuring agent has a melting point in a range of from about 50° C. to about 85° C.

Aspect 9 provides the pharmaceutical composition of Aspect 8, wherein the structuring agent has a melting point in a range of from about 60° C. to about 70° C.

Aspect 10 provides the pharmaceutical composition of Aspect 1, wherein the structuring agent comprises a monoglyceride, a diglyceride, a triglyceride, polyglyceride ester of a fatty acid, or a mixture thereof.

Aspect 11 provides the pharmaceutical composition of Aspect 1, wherein the structuring agent comprises tristearin, glyceryl distearate, glycerol monostearate, glyceryl dibehenate, cholesterol, trimyristin, glyceryl dimyristin, glyceryl monomyristin, trilaurin, glyceryl dilaurin, glyceryl monolaurin, tripalmitin, glyceryl dipalmitin, glyceryl monopalmitin, cholesterol, a polyglyceride ester of a fatty acid, a polyglycerol ester of a fatty acid, or a mixture thereof.

Aspect 12 provides the pharmaceutical composition of Aspect 11, wherein the structuring agent comprises glycerol monostearate, glyceryl distearate, tristearin, glycerol monopalmitin, glycerol dipalmitin, tripalmitin, glycerol monomyristin, glycerol dimyristin, trimyristin, or a mixture thereof.

Aspect 13 provides the pharmaceutical composition of Aspect 1, wherein the structuring agent is present in a concentration in a range of from about 0.1% (w/v) to about 25% (w/v) of the pharmaceutical composition based on the volume of the lipophilic oil.

Aspect 14 provides the pharmaceutical composition of Aspect 13, wherein the structuring agent is present in a concentration in a range of from about 3% (w/v) to about 20% (w/v) of the pharmaceutical composition based on the volume of the lipophilic oil.

Aspect 15 provides the pharmaceutical composition of Aspect 13, wherein the structuring agent is present in a concentration in a range of from about 3% (w/v) to about 10% (w/v) of the pharmaceutical composition based on the volume of the lipophilic oil.

Aspect 16 provides the pharmaceutical composition of Aspect 1, wherein the therapeutic agent comprises an analgesic agent, anesthetic agent, anti-inflammatory agent, a sympatholytic agent, an anxiolytic agent, a cannabinoid, or a mixture thereof dispersed in the lipophilic oil.

Aspect 17 provides the pharmaceutical composition of Aspect 16, wherein the analgesic agent, anesthetic agent, or both present in amount sufficient to reduce pain in a subject.

Aspect 18 provides the pharmaceutical composition of Aspect 17, wherein the pharmaceutical composition comprises the analgesic agent.

Aspect 19 provides the pharmaceutical composition of Aspect 18, wherein the analgesic agent comprises, a nonsteroidal anti-inflammatory drug, a COX-2 inhibitor, or a mixture thereof.

Aspect 20 provides the pharmaceutical composition of Aspect 19, wherein the nonsteroidal anti-inflammatory drug comprises ibuprofen, naproxen, diclofenac, mefenamic acid, indomethacin, cannabidiol, an ion pair thereof, a salt thereof, or a mixture thereof.

Aspect 21 provides the pharmaceutical composition of Aspect 19, wherein the COX-2 inhibitor comprises etoricoxib, meloxicam, celecoxib, an ion pair thereof, a salt thereof, or a mixture thereof.

Aspect 22 provides the pharmaceutical composition of Aspect 1, wherein the pharmaceutical composition comprises the anesthetic agent and the anesthetic agent is a local anesthetic.

Aspect 23 provides the pharmaceutical composition of Aspect 22, wherein the anesthetic agent comprises an ester-based local anesthetic, an amide-based local anesthetic, or a prodrug, or ion pair thereof, or salt thereof, or a mixture thereof.

Aspect 24 provides the pharmaceutical composition of Aspect 23, wherein the ester-based local anesthetic comprises procaine, amethocaine, benzocaine, tetracaine, or a prodrug, or ion pair thereof, or salt thereof, or a mixture thereof.

Aspect 25 provides the pharmaceutical composition of Aspect 23, wherein the local amide-based anesthetic comprises lidocaine, prilocaine, bupivacaine, levobupivacaine, ropivacaine, mepivacaine, dibucaine, etidocaine, a prodrug, or ion pair thereof, or salt thereof, or a mixture thereof.

Aspect 26 provides the pharmaceutical composition of Aspect 25, wherein the amide-based anesthetic comprises bupivacaine, ropivacaine, a salt thereof, ion pair thereof, or a mixture thereof.

Aspect 27 provides the pharmaceutical composition of Aspect 26, wherein the amide-based local anesthetic is an ion pair, or salt, comprising of bupivacaine butyrate, bupivacaine palmitate, bupivacaine laureate, bupivacaine myristate, bupivacaine stearate, bupivacaine hydroxystearate, bupivacaine oleate, bupivacaine ricinolate, bupivacaine docusate.

Aspect 28 provides the pharmaceutical composition of Aspect 1, wherein the pharmaceutical composition comprises a mixture of the analgesic agent, the anesthetic agent, and the anti-inflammatory agent.

Aspect 29 provides the pharmaceutical composition of Aspect 1, wherein the pharmaceutical composition comprises a mixture of the analgesic agent and the anesthetic agent.

Aspect 30 provides the pharmaceutical composition of Aspect 1, wherein the analgesic agent, anesthetic agent, or both are present in a concentration in a range of from about 2% (w/v) to about 15% (w/v) based on a volume of the lipophilic oil.

Aspect 31 provides the pharmaceutical composition of Aspect 30, wherein the analgesic agent, anesthetic agent, or both present in a concentration in a range of from about 3% (w/v) to about 10% (w/v) based on the volume of the lipophilic oil.

Aspect 32 provides the pharmaceutical composition of Aspect 1, wherein the anti-inflammatory agent comprises aspirin, celecoxib, diclofenac, diflunisal, etodolac, ibuprofen, indomethacin, ketoprofen, ketorolac, nabumetone, naproxen, oxaprozin, piroxicam, salsalate, sulindac, tolmetin, cannabidiol, a salt thereof, an ion pair thereof, or a mixture thereof a mixture thereof.

Aspect 33 provides the pharmaceutical composition of Aspect 1, further comprising an adjuvant.

Aspect 34 provides the pharmaceutical composition of Aspect 33, wherein the adjuvant comprises a corticosteroid, alpha-2-agonist, pethidine, barbiturate, opiate, tubocurarine chloride, a cannabinoid, meloxicam a salt thereof, or ion pair thereof, or a mixture thereof.

Aspect 35 provides the pharmaceutical composition of Aspect 34, wherein the cannabinoid is cannabidiol (CBD).

Aspect 36 provides the pharmaceutical composition of Aspect 33, wherein the pharmaceutical composition is effective at relieving pain in a subject using a smaller concentration of the analgesic agent, anesthetic agent, an anti-inflammatory agent, or mixture thereof and/or has a longer pain relieving effect, compared to a corresponding pharmaceutical composition that is free of the adjuvant.

Aspect 37 provides the pharmaceutical composition of Aspect 1, further comprising a rheological modifier comprising C2-C12-alcohol.

Aspect 38 provides the pharmaceutical composition of Aspect 37, wherein the rheological modifier comprises ethanol, benzyl alcohol, or a mixture thereof.

Aspect 39 provides the pharmaceutical composition of Aspect 38, wherein the C2-C12 alcohol comprises ethanol, benzyl alcohol, or a mixture thereof and is present in a range of from about 0.5% (w/v) to about 10% (w/v) of the pharmaceutical composition based on the volume of the lipophilic oil.

Aspect 40 provides the pharmaceutical composition of Aspect 39, wherein the ethanol, benzyl alcohol, or a mixture thereof is present in a range of from about 1% (w/v) to about 6% (w/v) of the pharmaceutical composition based on the volume of the lipophilic oil.

Aspect 41 provides the pharmaceutical composition of Aspect 1, wherein the pharmaceutical composition is effective to reduce pain in a subject for a time in a range of from about 24 hours to about 14 days.

Aspect 42 provides the pharmaceutical composition of Aspect 1, wherein the pharmaceutical composition is effective to reduce pain in a subject for a time in a range of from about 48 hours to about 96 hours.

Aspect 43 provides the pharmaceutical composition of Aspect 1, wherein the pharmaceutical composition is effective to reduce pain in a subject for a time in a range of from about 96 hours to about 168 hours.

Aspect 44 provides the pharmaceutical composition of Aspect 1, wherein the pharmaceutical composition is effective to reduce pain in a subject for a time in a range of from about 168 hours to about 336 hours.

Aspect 45 provides the pharmaceutical composition of Aspect 1, wherein the pharmaceutical composition is a semi-solid composition.

Aspect 46 provides a pharmaceutical composition, comprising:
a medium-chain triglyceride;
a castor oil;
an anesthetic agent comprising bupivacaine, an ion pair thereof, or salt thereof, or both and present in amount sufficient to reduce pain in a subject, and dispersed about the medium-chain triglyceride and castor oil mixture; and
a structuring agent comprising tristearin, glyceryl distearate, glycerol monostearate, glyceryl dibehenate, cholesterol, trimyristin, glyceryl dimyristin, glyceryl monomyristin, trilaurin, glyceryl dilaurin, glyceryl monolaurin, tripalmitin, glyceryl dipalmitin, glyceryl monopalmitin, cholesterol, a polyglyceride ester of a fatty acid, a polyglycerol ester of a fatty acid, or a mixture thereof, wherein
optionally a wt:wt ratio of the medium-chain triglyceride to castor oil is about 50:50.

Aspect 47 provides the pharmaceutical composition of Aspect 1, wherein a viscosity of the composition is in a range of from about 10,000 cP to about 1,000,000 cP, when measured at about 37° C.

Aspect 48 provides the pharmaceutical composition of Aspect 1, wherein a viscosity of the composition is in a range of from about 10,000 cP to about 150,000 cP, when measured at about 37° C.

Aspect 49 provides the pharmaceutical composition of Aspect 1, wherein following shearing, a viscosity of the composition is in a range of from about 10 cP to about 10,000 cP when measured at about 37° C.

Aspect 50 provides the pharmaceutical composition of Aspect 1, wherein following shearing, the viscosity reduces to allow injectability by a shear-thinning behavior.

Aspect 51 provides a kit comprising:
a syringe; and
the pharmaceutical composition of Aspect 1, disposed within the syringe.

Aspect 52 provides the kit of Aspect 51, wherein the pharmaceutical composition is sealed within the syringe.

Aspect 53 provides the kit of Aspect 51, wherein the syringe further comprises a needle having a size of about 15-30 gauge.

Aspect 54 provides the kit of Aspect 53, wherein the syringe comprises a needle size of about 21 to about 25 gauge.

Aspect 55 provides a method of manufacturing the pharmaceutical composition of Aspect 1, the method comprising:
a) mixing the lipophilic oil and the analgesic agent, anesthetic agent under stirring and heating at a temperature above 25° C. to form a mixture;
b) cooling the mixture to form the pharmaceutical composition.

Aspect 56 provides the method of Aspect 55, wherein mixing at a) is conducted at a temperature in a range of from about 50° C. to about 150° C.

Aspect 57 provides the method of Aspect 56, wherein the mixture is placed in a sealed syringe to cool at b).

Aspect 58 provides the method of Aspect 57, further comprising sterilizing the pharmaceutical composition.

Aspect 59 provides the method of Aspect 58, wherein sterilization occurs after the pharmaceutical composition is sterilized after it is dispensed in a container, wherein sterilization comprises gamma irradiation, electron beam irradiation, x-ray irradiation, heat sterilization, steam sterilization, or a combination thereof.

Aspect 60 provides a method of treating a subject with the pharmaceutical composition of Aspect 1, comprising administering the pharmaceutical composition to the subject in need thereof.

Aspect 61 provides the method of Aspect 60, wherein the pharmaceutical composition is administered to the subject at or proximate to a surgical site.

Aspect 62 provides the method of Aspect 61, wherein the pharmaceutical composition is administered to the subject at or proximate to a wound.

Aspect 63 provides the method of Aspect 62, wherein the pharmaceutical compositions is administered to a subject at a site that is proximal to a wound.

Aspect 64 provides the method of Aspect 63, wherein the site proximal to the wound is a site that results in a nerve or nerves being blocked.

Aspect 65 provides the method of Aspect 61, wherein a first portion of the pharmaceutical composition is administered to the subject at or proximate to the wound and a second portion of the pharmaceutical composition is administered to the subject at a site proximal to the wound.

Aspect 66 provides the method of Aspect 61, wherein administering the pharmaceutical composition comprises injecting the pharmaceutical composition through a syringe, through a needle having a size of about 18-30 gauge, rubbing the pharmaceutical composition at or proximate to a wound or surgical site, or a combination thereof.

Aspect 67 provides the method of Aspect 62, wherein the pharmaceutical composition is administered to the subject before surgery is performed, during surgery, or after the subject has had surgery performed.

Aspect 68 provides the method of Aspect 67, further comprising administering a non-opioid analgesic agent to the subject 48 to 120 hours after the pharmaceutical composition is administered to the subject.

Aspect 69 provides the method of Aspect 68, further comprising administering a non-opioid analgesic agent to the subject 72 to 120 hours after the pharmaceutical composition is administered to the subject.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range. The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than or equal to about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

What is claimed is:

1. An injectable pharmaceutical composition, comprising:
   bupivacaine in a range of from about 3 wt % to about 7 wt % of the pharmaceutical composition;
   medium-chain triglyceride oil in a range of from about 39.5 wt % to about 46.5 wt % of the pharmaceutical composition;
   a castor oil in a range of from about 39.5 wt % to about 46.5 wt % of the pharmaceutical composition; and
   tristearin in a range of from about 0.5 wt % to about 6 wt % of the pharmaceutical composition, wherein
   the pharmaceutical composition is free of a rheological modifier and
   a wt:wt ratio of the medium-chain triglyceride to castor oil is about 50:50.

2. The injectable pharmaceutical composition of claim 1, wherein the injectable pharmaceutical composition is a nerve block composition.

3. A kit comprising:
   a syringe comprising a needle having a size of about 15-30 gauge; and
   the injectable pharmaceutical composition of claim 1, disposed and sealed within the syringe.

4. A method of manufacturing the pharmaceutical composition of claim 1, the method comprising:
   a) mixing the bupivacaine, medium-chain triglyceride oil, castor oil and tristearin, anesthetic agent under stirring and heating at a temperature above 25° C. and up to 150° C. to form a mixture;
   b) placing the mixture in a sealed syringe and cooling the mixture to form the pharmaceutical composition; and
   c) sterilizing the pharmaceutical composition, wherein sterilization occurs after the pharmaceutical composition placed in the sealed syringe, wherein sterilization comprises gamma irradiation, electron beam irradiation, x-ray irradiation, heat sterilization, steam sterilization, or a combination thereof.

5. A method of treating pain in a subject in need thereof, with the pharmaceutical composition of claim 1, comprising administering the pharmaceutical composition to the subject in need thereof, wherein the pharmaceutical composition is administered to the subject before surgery is performed, during surgery, or after the subject has had surgery performed, and administering the pharmaceutical composition comprises injecting the pharmaceutical composition through a syringe, through a needle having a size of about 18-30 gauge, at or proximate to a wound or surgical site.

* * * * *